(12) United States Patent
Puckett

(10) Patent No.: US 11,944,707 B2
(45) Date of Patent: Apr. 2, 2024

(54) DUAL RELEASE DOSAGE FORM CAPSULE AND METHODS, DEVICES AND SYSTEMS FOR MAKING SAME

(71) Applicant: Gel Cap Technologies, LLC, Ferndale, WA (US)

(72) Inventor: John Puckett, Custer, WA (US)

(73) Assignee: Gel Cap Technologies, LLC, Ferndale, WA (US)

( * ) Notice: Subject to any disclaimer, the term of this patent is extended or adjusted under 35 U.S.C. 154(b) by 1068 days.

(21) Appl. No.: 16/448,074

(22) Filed: Jun. 21, 2019

(65) Prior Publication Data

US 2019/0307699 A1 Oct. 10, 2019

Related U.S. Application Data

(62) Division of application No. 16/031,821, filed on Jul. 10, 2018, now Pat. No. 10,376,471.

(Continued)

(51) Int. Cl.
*A61K 9/48* (2006.01)
*A61J 3/07* (2006.01)
(Continued)

(52) U.S. Cl.
CPC .............. *A61K 9/4808* (2013.01); *A61J 3/07* (2013.01); *A61J 3/074* (2013.01); *A61J 3/077* (2013.01);
(Continued)

(58) Field of Classification Search
CPC .... A61J 3/07; A61J 3/072; A61J 3/074; A61J 3/077; A61K 9/4808; A61K 9/4816;
(Continued)

(56) References Cited

U.S. PATENT DOCUMENTS

| 1,510,260 A | * | 9/1924 | Cyrenius | ................. | A61J 3/071 |
| | | | | | 206/508 |
| 2,309,545 A | * | 1/1943 | Scherer | .................... | A61J 3/07 |
| | | | | | 53/553 |

(Continued)

FOREIGN PATENT DOCUMENTS

| CN | 101827571 | 9/2010 |
| CN | 101827586 | 9/2010 |

(Continued)

OTHER PUBLICATIONS

WO, International Search Report and Written Opinion; International Application No. PCT/US2018/041516 (dated Oct. 2, 2018).‡

(Continued)

*Primary Examiner* — Robert F Long
*Assistant Examiner* — Eduardo R Ferrero
(74) *Attorney, Agent, or Firm* — FisherBroyles, LLP; Susan M. Oiler

(57) ABSTRACT

Capsule forming machines that form a dual dosage capsule have superimposed upper and lower plates that are each rotatable about an axis of rotation. Each of the upper and lower plates define a plurality of voids for receiving a shell body or a capsule member of a capsule that are positioned to define a plurality of stations. A first distribution device is operatively positioned at one of the plurality of stations of each of the upper and lower plates and an actuator is operatively connected to either of the upper or lower plates. The actuator lifts and lowers the upper plate or the lower plate relative to the other plate and/or pivots the upper plate or the lower plate relative to the other plate transverse to the rotational axis to move a capsule assembly station thereof toward to the other plate and then away from the other plate at predetermined times.

11 Claims, 8 Drawing Sheets

Related U.S. Application Data

(60) Provisional application No. 62/530,658, filed on Jul. 10, 2017.

(51) Int. Cl.
*A61K 31/00* (2006.01)
*A61K 45/06* (2006.01)

(52) U.S. Cl.
CPC .......... *A61K 9/4833* (2013.01); *A61K 9/4858* (2013.01); *A61K 9/4891* (2013.01); *A61K 31/00* (2013.01); *A61K 45/06* (2013.01); *A61K 9/4816* (2013.01)

(58) Field of Classification Search
CPC .... A61K 9/4891; A61K 31/00; A61K 35/741; A61K 45/06; Y10S 53/90; B65B 43/60; B65B 3/003
USPC ...................................................... 53/137.2
See application file for complete search history.

(56) References Cited

U.S. PATENT DOCUMENTS

| | | | | |
|---|---|---|---|---|
| 2,340,037 A * | 1/1944 | Zipper | A61J 3/071 | 206/530 |
| 2,349,511 A * | 5/1944 | Miller | A61J 3/07 | 264/145 |
| 3,070,932 A * | 1/1963 | Hofliger | A61J 3/074 | 53/900 |
| 3,186,910 A * | 6/1965 | Glassman | A61J 3/071 | 424/435 |
| 3,228,789 A * | 1/1966 | Glassman | A61K 9/4891 | 427/399 |
| 3,264,802 A * | 8/1966 | Kath | A61J 3/077 | 53/140 |
| 3,399,803 A * | 9/1968 | Oglevee | A61J 3/071 | 426/138 |
| 3,518,340 A * | 6/1970 | Dick | A61J 3/071 | 264/254 |
| 3,675,390 A * | 7/1972 | Austin | B65B 43/60 | 53/201 |
| 3,823,816 A | 7/1974 | Controulis et al. | | |
| 4,403,461 A * | 9/1983 | Goutard | B65B 51/02 | 53/900 |
| 4,450,877 A * | 5/1984 | Walker | A61K 9/4866 | 141/1 |
| 4,478,658 A * | 10/1984 | Wittwer | A61K 9/4883 | 53/399 |
| 4,487,327 A * | 12/1984 | Grayson | A61J 3/071 | 220/8 |
| 4,543,138 A * | 9/1985 | Bollinger | A61J 3/072 | 206/530 |
| 4,550,238 A * | 10/1985 | Van Herle | B29C 66/93451 | 219/121.64 |
| 4,576,284 A * | 3/1986 | Wittwer | B29C 65/56 | 426/138 |
| 4,724,019 A * | 2/1988 | Brown | B29C 65/4895 | 209/543 |
| 4,738,724 A * | 4/1988 | Wittwer | B29C 66/24221 | 106/206.1 |
| 4,738,817 A * | 4/1988 | Wittwer | B29C 66/53423 | 524/24 |
| 4,793,119 A * | 12/1988 | Maso | A61J 3/072 | 53/329.2 |
| 4,793,493 A * | 12/1988 | Makiej, Jr. | A61J 3/071 | 424/467 |
| 4,820,364 A * | 4/1989 | Graham | A61J 3/072 | 156/305 |
| 4,899,516 A * | 2/1990 | Krieger | A61J 3/072 | 118/317 |
| 4,922,682 A * | 5/1990 | Tait | A61J 3/072 | 53/329.3 |
| 4,936,074 A * | 6/1990 | Graham | A61K 9/4866 | 53/900 |
| 4,936,461 A * | 6/1990 | Makiej, Jr. | A61K 9/4808 | 424/467 |
| RE33,251 E * | 7/1990 | Wittwer | B29C 66/9161 | 156/305 |
| 4,964,262 A * | 10/1990 | Moser | A61J 3/074 | 53/506 |
| 4,991,377 A * | 2/1991 | Marchesini | A61J 3/072 | 53/375.9 |
| 5,054,258 A * | 10/1991 | Tait | A61J 3/072 | 198/803.14 |
| 5,074,426 A * | 12/1991 | Goodhart | A61J 3/071 | 220/4.24 |
| 5,081,822 A * | 1/1992 | Boyd | A61J 3/074 | 53/485 |
| 5,312,388 A * | 5/1994 | Wong | A61K 9/0004 | 604/892.1 |
| 5,314,696 A * | 5/1994 | Paulos | A61J 3/07 | 424/463 |
| 5,387,421 A ‡ | 2/1995 | Amidon | A61K 9/0004 | 424/45 |
| 5,538,959 A * | 7/1996 | Mauskop | A61K 33/14 | 514/224.5 |
| 5,770,224 A * | 6/1998 | Rashid | A61K 9/4808 | 220/8 |
| 5,930,984 A * | 8/1999 | Furuya | A61J 3/072 | 53/485 |
| 6,050,308 A * | 4/2000 | Wurst | G01F 11/24 | 141/81 |
| 6,120,802 A * | 9/2000 | Breitenbach | A61K 31/277 | 424/464 |
| 6,367,228 B1 * | 4/2002 | Wurst | A61J 3/074 | 53/53 |
| 6,949,154 B2 * | 9/2005 | Hochrainer | B29C 66/9161 | 53/900 |
| 7,163,693 B1 * | 1/2007 | Clarke | A61J 3/07 | 424/452 |
| 7,812,039 B2 * | 10/2010 | Del Soldato | A61K 31/7024 | 514/357 |
| 7,883,721 B2 * | 2/2011 | McAllister | A61K 9/4808 | 424/400 |
| 8,303,461 B2 * | 11/2012 | Griffin | F16C 33/6677 | 475/331 |
| 8,361,497 B2 * | 1/2013 | Miller | A61K 9/4833 | 424/400 |
| 8,569,375 B2 * | 10/2013 | Campbell | A61K 9/0056 | 514/570 |
| 8,968,717 B2 * | 3/2015 | McInnes | A61J 3/071 | 424/85.4 |
| 9,340,004 B2 * | 5/2016 | Van Rooyen | A61K 9/4808 | |
| 10,046,549 B2 * | 8/2018 | Van Rooyen | B32B 38/18 | |
| 10,376,471 B2 * | 8/2019 | Puckett | A61K 31/00 | |
| 2003/0194431 A1 * | 10/2003 | Miller | A61K 9/4866 | 424/451 |
| 2004/0144066 A1 * | 7/2004 | Piemontese | A61J 3/072 | 53/485 |
| 2004/0166153 A1 * | 8/2004 | McAllister | A61K 9/4816 | 424/452 |
| 2005/0217207 A1 * | 10/2005 | Konishi | A61J 3/074 | 53/53 |
| 2006/0034913 A1 * | 2/2006 | Gaede | A61K 9/006 | 424/464 |
| 2006/0057201 A1 * | 3/2006 | Bonney | A61J 3/071 | 424/471 |
| 2006/0157054 A1 * | 7/2006 | Kuehn | A61M 15/0028 | 128/200.23 |
| 2007/0065501 A1 * | 3/2007 | He | A61K 9/4808 | 514/57 |
| 2007/0065502 A1 * | 3/2007 | Baksh | A61K 9/4883 | 424/754 |
| 2007/0087048 A1 * | 4/2007 | Abrams | A61J 3/071 | 424/456 |
| 2007/0087049 A1 ‡ | 4/2007 | Clarke | A61J 3/07 | 424/45 |

(56) References Cited

U.S. PATENT DOCUMENTS

| | | | | |
|---|---|---|---|---|
| 2007/0298095 | A1* | 12/2007 | Nagata | A61K 9/4816 514/781 |
| 2008/0008750 | A1* | 1/2008 | Tochio | A61K 9/4816 424/454 |
| 2008/0141621 | A1* | 6/2008 | Funaro | A61J 3/072 53/138.1 |
| 2008/0200549 | A1* | 8/2008 | Atkinson | A61K 31/215 514/529 |
| 2008/0254111 | A1* | 10/2008 | Tochio | A61J 3/072 528/425 |
| 2008/0275125 | A1* | 11/2008 | Atkinson | A61K 31/167 514/576 |
| 2008/0299188 | A1* | 12/2008 | Appel | A61K 9/0004 424/490 |
| 2009/0108492 | A1* | 4/2009 | McAllister | A61J 3/077 425/542 |
| 2009/0110723 | A1‡ | 4/2009 | McAllister | A61J 3/071 424/45 |
| 2009/0148514 | A1* | 6/2009 | Matthews | A61K 9/4808 424/451 |
| 2009/0241482 | A1* | 10/2009 | Yagyu | B65B 35/08 53/540 |
| 2010/0018167 | A1* | 1/2010 | McCutcheon | A61J 3/072 53/329.2 |
| 2010/0119597 | A1‡ | 5/2010 | Clarke | A61J 3/07 424/45 |
| 2010/0212261 | A1* | 8/2010 | Boldis | A61J 3/074 53/403 |
| 2010/0327476 | A1* | 12/2010 | Spallek | A61J 3/074 264/85 |
| 2011/0124730 | A1* | 5/2011 | Atkinson | A61K 9/0095 514/570 |
| 2011/0146843 | A1‡ | 6/2011 | Ansaloni | A61J 3/074 141/36 |
| 2011/0166234 | A1* | 7/2011 | Atkinson | A61P 19/00 514/570 |
| 2011/0275718 | A1* | 11/2011 | Atkinson | A61K 31/16 514/570 |
| 2011/0277300 | A1* | 11/2011 | Hirota | A61J 3/074 29/428 |
| 2013/0186561 | A1* | 7/2013 | Van Rooyen | A61J 3/072 156/292 |
| 2013/0225685 | A1* | 8/2013 | Atkinson | A61K 9/0019 514/570 |
| 2014/0073696 | A1* | 3/2014 | Atkinson | A61K 31/215 514/570 |
| 2014/0221494 | A1* | 8/2014 | Atkinson | A61K 31/137 514/629 |
| 2014/0302133 | A1* | 10/2014 | Van Rooyen | A61K 9/4808 424/453 |
| 2017/0087104 | A1* | 3/2017 | Atkinson | A61P 11/02 |
| 2018/0014999 | A1* | 1/2018 | Larimer | B65B 43/44 |
| 2018/0264798 | A1* | 9/2018 | Van Rooyen | A61J 3/072 |
| 2019/0008781 | A1* | 1/2019 | Puckett | A61K 31/00 |
| 2019/0307699 | A1* | 10/2019 | Puckett | A61J 3/074 |

FOREIGN PATENT DOCUMENTS

| | | |
|---|---|---|
| CN | 203736555 | 7/2014 |
| EP | 0225565 A2 | 6/1987 |
| WO | WO-2006024949- ‡ | 3/2006 |

OTHER PUBLICATIONS

EP, Extended Search Report; Application No. 18832563.3 (dated Mar. 19, 2021) (7 pages).
CN, 1st Office Action English Translation; Application No. 2018800553877 (dated Sep. 2, 2020) (9 pages).
CN, 2nd Office Action English Translation; Application No. 2018800553877 (dated Mar. 18, 2021) (12 pages).
JP, 1st Office Action English Translation, Application No. 2020-523680 (dated Feb. 4, 2022) (7 pages).
JP, 2nd Office Action English Translation, Application No. 2020-523680, (dated May 31, 2022) (4 pages).
IN, Examination Report, Application No. 202027005267 (dated Mar. 25, 2022) (7 pages).
CN, 3rd Office Action English Translation, Application No. 2018800553877 ( dated Aug. 10, 2021) (12 pages).

* cited by examiner
‡ imported from a related application

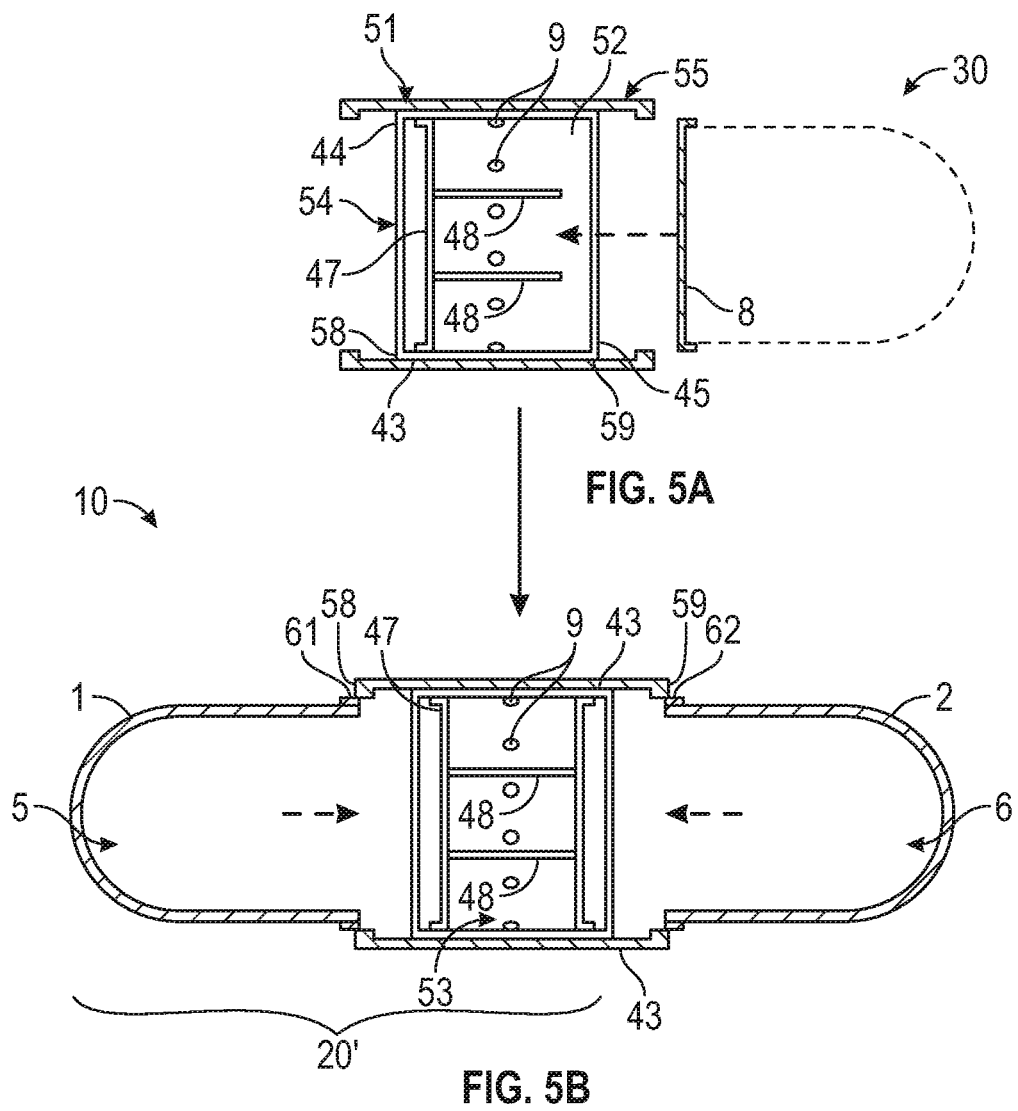
FIG. 5A
FIG. 5B
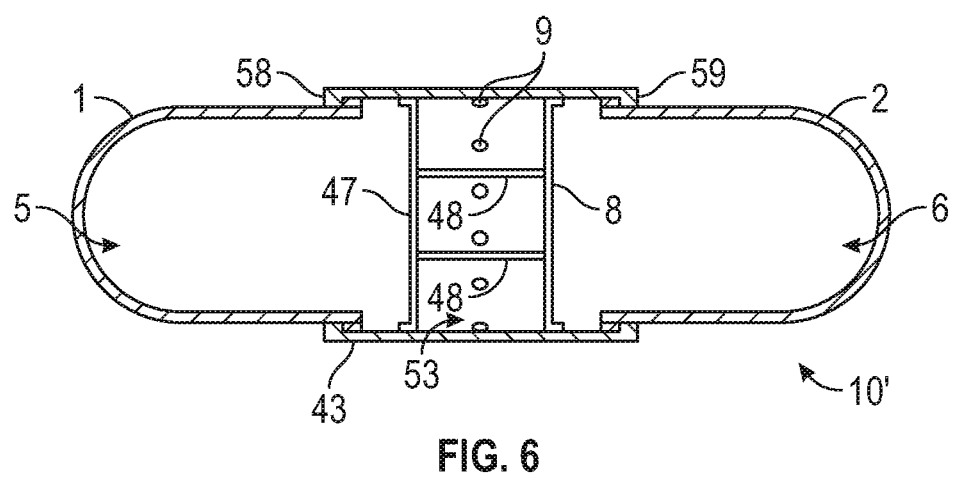
FIG. 6

DUAL RELEASE DOSAGE FORM CAPSULE AND METHODS, DEVICES AND SYSTEMS FOR MAKING SAME

RELATED APPLICATIONS

This application is a divisional of U.S. application Ser. No. 16/031,821, filed Jul. 10, 2018, which claims the benefit of U.S. Provisional Application 62/530,658, filed Jul. 10, 2017, the entirety of which is incorporated herein by reference.

TECHNICAL FIELD

The present disclosure relates generally to the field of capsules, and in particular a dual release dosage form capsule. The present disclosure also relates to methods, devices and systems for manufacturing dual release dosage capsules.

BACKGROUND

Conventional capsules for pharmaceuticals or other powdered, granular or liquid substances, are two-piece capsules having telescoping bodies. For example, the bodies are generally tubular-shaped having a closed end and an open end. One body is generally larger than the diameter of the other body so that the open end of the larger body can at least partially be slipped over the smaller diameter body. The bodies can be tightly fitted, for example, so that the fill material inside the capsule does not leak out. In some capsules a band may be used to secure the two bodies together.

While such two-piece capsules are known, the design of the conventional two-piece capsule has several limitations and disadvantages. In liquid filled capsules, for example, the cavity within the capsule can include only a single mixture. Hence, different active ingredients that interact with each other, for example, cannot be included within the same capsule. In other words, the capsule is limited to the delivery of only internally compatible ingredients. Further, the contents of the conventional capsule are released at once when the capsule dissolves. Hence, there is no way to alter or modify the release time of the same or different drugs. There are also limited ways to mix incompatible ingredients.

To address these issues, others have developed dosage form capsules that have at least one smaller capsule stored within (inside) a larger capsule. Generally, such capsules require a larger two-piece capsule forming the outer shell of the dosage form and one or more smaller capsules therein storing different mediums. Disadvantages of this arrangement include size limitations of the capsules. For example, the inner capsule has a smaller volume than the outer capsule. Further, the outer capsule can be difficult to swallow if its volume is too large. It can also be difficult to manufacture the capsule-within-a-capsule design. Other attempts to address the limitations of the conventional two-piece capsule include the use of solid particles that are dispersed within a liquid capsule fill. The particles, for example, may be coated with one or more substances to protect them from the liquid component and/or to alter their release rate. Among other limitations, however, such solid/liquid fills are inherently expensive to manufacture. Further, not all drugs are available in solid form and/or amenable to coating.

Therefore, there remains a need for a capsule that overcomes the problems of the conventional capsule. More particularly, there remains a need for a dosage form capsule that provides a dual release of the same or different fill materials at the same and/or different times. There further remains a need for a dosage form capsule that permits the delivery of otherwise incompatible fill materials and active ingredients. There also remains a need for a dual release dosage form capsule that simplifies assembly and filling processes of the capsule.

SUMMARY

In all aspects described herein, a dual dosage form capsule is provided, which may be a dual release capsule. The dual dosage form capsule has a first end or capsule member filled with a first fill material and a second end or capsule member filled with a second fill material, which may be the same or different materials. A first end of a band is connected to the first capsule member to sealingly contain the first fill material therein and an opposing second end connected to the second capsule member to sealingly contain the second fill material therein. This construction defines an internal chamber between the first capsule member and the second capsule member within the band. The band includes one or more apertures therethrough radially oriented relative to a longitudinal axis of the capsule, thereby placing the internal chamber in fluid communication with the environment outside the capsule.

In multiple embodiments, the first end of the annular band is open and has an end of the first capsule member received therein and the second end of the annular band is open and has an end of the second capsule member received therein. The end of the first capsule member received in the annular band has a cap sealingly closing the end of the first capsule member and the cap is seated within the band, and the end of the second capsule member received in the annular band has a cap sealingly closing the end of the second capsule member and the cap is seated within the band.

In another embodiment, the first end of the annular band is open and has an end of the first capsule member received therein and the second end of the annular band is open and has an end of the second capsule member received therein. Here, the annular band includes a cover therein for sealingly closing the end of the second capsule member and an open opposing end receiving the end of the first capsule member, which is sealingly closed by a cap. Alternately, the band can be a two-part construction, a first annular band portion having a cover for the first capsule member integral therewith and a second annular band portion having a cover for the second capsule member integral therewith. The first annular band portion and the second annular band portion each have an open end opposite the cover therein and the open ends are connectable to one another to form the band and either or both have the plurality of apertures therethrough. An in yet another embodiment, the annular band includes a cover therein for sealingly closing the end of the second capsule member and for sealingly closing the end of the first capsule member.

In other embodiments, the first end of the annular band is received in an open end of the first capsule member and the second end of the annular band is received in an open end of the second capsule member. Here, the annular band includes a cover therein for sealingly closing the end of the second capsule member and for sealingly closing the end of the first capsule member. Alternately, the band can be a two-part construction, a first annular band portion having a cover for the first capsule member integral therewith and a second annular band portion having a cover for the second capsule member integral therewith. The first annular band portion and the second annular band portion each have an open end opposite the cover therein and the open ends are connectable to one another to form the band and either or both have the plurality of apertures therethrough.

In certain example embodiments, the dual release dosage form capsule includes a first capsule member having a first fill material and a second capsule member having a second fill material. A band couples the first capsule member to the second capsule member and forms a third chamber defined by an inner surface of the band and a cap of the capsule members. An aperture in the band places the third chamber in fluid communication with the environment outside of the capsule. When the capsule is swallowed, for example, digestive fluid can enter the third chamber through the aperture, thereby exposing the capsule members to the fluid. In certain aspects, fluid movement into the third chamber causes the band to at least partially dissolve so that caps of the capsule members are exposed.

In all aspects, the first fill material and the second fill material can be released from the capsule at different times, thus enabling a dual timing release of the fill materials or can be released from the capsule at substantially the same time enabling the first and second fill materials to interact for the first time upon being released from the capsule.

In certain example aspects described herein, a process for manufacturing a dual release dosage form capsule is provided, including devices and systems for making the dual release dosage capsules described herein. The process for manufacturing a dual release dosage form capsule includes providing materials to a capsule body filling device that is configured to fill and seal fill materials into a shell body to form a sealed capsule member. In another aspect, the process for manufacturing a dual release dosage form capsule includes providing sealed capsule members and/or a combination of a capsule member and a shell body to a capsule forming device. The capsule forming device can be sized and configured to couple two capsule members together with a band to form the capsule.

The capsule forming machine has superimposed upper and lower plates that are each rotatable about an axis of rotation. Each of the upper and lower plates define a plurality of voids for receiving a shell body or a capsule member of a capsule and the plurality of voids are positioned to define a plurality of stations. A first distribution device is operatively positioned at one of the plurality of stations of each of the upper and lower plates. An actuator is operatively connected to either of the upper or lower plates and lifts and lowers the upper or lower plate relative to the other plate and/or pivots the upper or lower plate relative to the other plate transverse to the rotational axis to move a capsule assembly station thereof toward to the other plater and then away from the other plate at predetermined times. The first distribution device distributes shell bodies or capsule members to a first station. In all aspects, a second distribution device distributes a fill material when the first distribution device distributes shell bodies or distributes bands when the first distribution device distributes capsules members having a cap sealing enclosing a fill material therein. In one embodiment, the first distribution device of the lower plate distributes first capsules members having a first band portion sealing enclosing a first fill material therein and the first distribution device of the upper plate distributes second capsule members having a second band portion sealing enclosing a second fill material therein, and at the capsule assembly station the first band portion and the second band portion are mated together to form a capsule. The machine also includes a sealing device operatively positioned at either the capsule assembly station or a station subsequent to the capsule assembly station.

A method of providing a dual release of one or more active ingredients is provided. The method includes exposing the dual release dosage form capsule describe herein to a fluid. Upon exposure to the fluid, a first release of at least a portion of the first fill material occurs from the dual release dosage form capsule before a second release of at least a portion of the second fill material. Similarly, a method of providing a dual release of one or more active ingredients in a subject is provided as described herein. The method includes, for example, administering to the subject the dual release dosage form capsule described herein, such as by oral consumption. Such administration of the dual release dosage form capsule results in a first release of at least a portion of the first fill material from the dual release dosage form capsule before a second release of at least a portion of the second fill material. The second release occurs at least one hour after the first release.

These and other aspects, objects, features, and advantages of the example embodiments will become apparent to those having ordinary skill in the art upon consideration of the following detailed description of illustrated example embodiments. Related methods of operation are also provided. Other apparatuses, methods, systems, features, and advantages of the dual release dosage form capsule, and process for making the capsule, will be or become apparent to one with skill in the art upon examination of the following figures and detailed description. It is intended that all such additional apparatuses, methods, systems, features, and advantages be included within this description, be within the scope of dual release dosage form capsule, and process for making the capsule, be protected by the accompanying claims.

BRIEF DESCRIPTION OF THE DRAWINGS

FIG. 5A is a cross-sectional view of one embodiment of a band that can receive a cap or a cap and capsule member.

FIG. 5B is a cross-sectional exploded view of the band of FIG. 5A having received a cap and about to receive a first and second capsule member.

FIG. 6 is a cross-sectional view of the assembled capsule of FIG. 5B.

DETAILED DESCRIPTION

Figure 1:
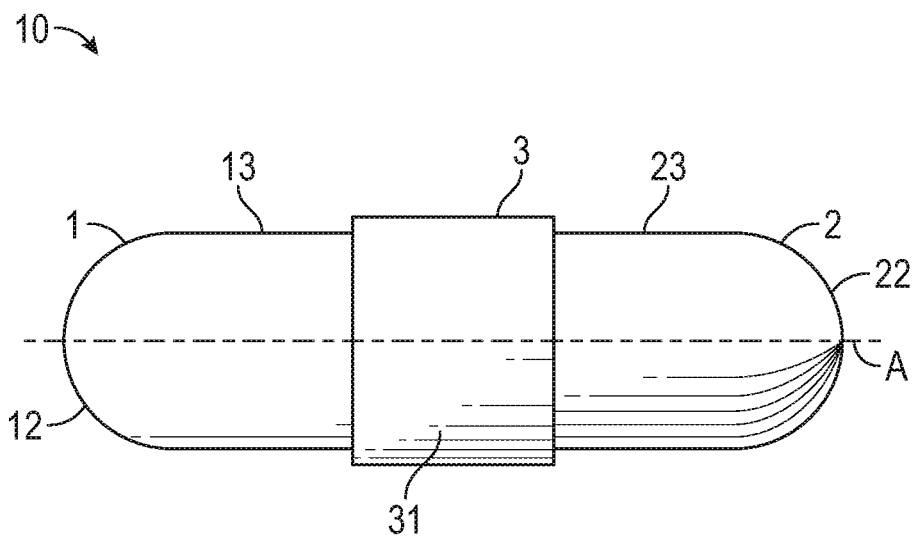
FIG. 1 is a side view of a dual release dosage form capsule, in accordance with certain example embodiments.

Provided herein is a dual release dosage form capsule, along with a process for manufacturing the dual release dosage form capsule. The dual dosage form capsule includes two capsule halves, each of which are capped on one end to form a capsule member. Each capsule member, for example, can be filled with a different fill material. A band is used to couple the two capsule members together, thereby forming the dual dosage form capsule. Application of the band to the capsule members forms a chamber between the capsule members, the chamber being contiguous with the exterior surfaces of the capsule member caps and the interior surface of the band. The band includes one or more apertures, thus exposing the third chamber to the environment. The apertures, for example, permit fluid movement into the chamber between the capsule members, thereby facilitating release of the fill materials in a predetermined fashion.

More particularly, in certain examples the caps of each capsule member can be made of different materials, such as materials that dissolve at different rates. Additionally or alternatively, the caps can be configured differently so that they dissolve at different rates, thereby releasing the fill material at different rates. For example, one cap may be thicker than the cap of the other capsule member, thus increasing the dissolve time for the thicker cap and hence delaying the release of the active ingredient covered by the thicker cap. The thickness of the cap may be in a range from 0.25 mm to 1.5 mm, more preferably 0.5 mm to 1 mm.

In all embodiments, the band is also made of a dissolvable material, such that the band also dissolves when the dual dosage form capsule is swallowed and exposed to digestive fluids. In particular, the apertures act as perforations in the band to provide a point of weakness upon which the digestive fluids will act to divide the capsule in half and/or enable digestive fluids access to the caps.

These and other features of the dual release dosage form capsule advantageously permit the timed release of active ingredients from a single dosage form. That is, the dual release capsule described herein allows a dual timing release so that a first fill material positioned in a portion of the capsule can be released at a different time than a second fill material positioned in a second portion of the capsule. For example, a first pharmaceutical, such as ibuprofen, can be positioned in the capsule and released at a first time, and a second pharmaceutical, such as acetaminophen, can be positioned in the capsule and released at a second time that is different than the first time. When the capsule is ingested, the ibuprofen and acetaminophen are thus released at different times. Hence, in this example, a longer duration of pain management can be achieved from a single dosage form, as compared to taking ibuprofen or acetaminophen alone in separate dosage forms. The dosage form, for example, can be a modified release dosage form, a sustained release dosage form, a controlled-release dosage form, or extended release dosage form.

In certain examples, the dual release capsule described herein allows a substantially simultaneous release of at least two fill materials, the fill materials otherwise being generally incompatible if mixed together. For example, if two pharmaceutical agents undesirably interact thereby shortening shelf life, a first pharmaceutical agent can be positioned in a first portion of the dual release dosage form and a second pharmaceutical agent can be positioned in a separate, second portion of the dosage form. In this example, the first and second pharmaceutical agents can be released from the capsule at substantially the same time, such as when ingested, but otherwise maintained separately before ingestion. Hence, in certain examples the dual dosage form described herein advantageously increases shelf life.

The dual release dosage capsule form can be made in a variety of ways. In certain examples, the capsule members can be formed separately and then joined together with a band. For example, a capsule body filling device can be used to fill the capsule halves and to form the two capsule members by application of a cap to each capsule halve. A capsule forming device can then be used to couple the capsule members together with the band, thereby forming the dual release dosage form capsule described herein. The band, for example, can be a pre-formed band that includes one or more apertures.

The invention will now be described in detail by way of reference only using the following definitions and examples. All patents and publications referred to herein are expressly incorporated by reference in their entirety. It is to be understood that one, some or all of the properties of the various embodiments described herein may be combined to form other embodiments of the present invention. Further, the section headings used herein are for organizational purposes only and are not to be construed as limiting the subject matter described.

The terms used herein generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms are highlighted in quotation marks. The use of such highlighting has no influence on the scope and meaning of a term. Rather, the scope and meaning of a term is the same, in the same context, whether or not it is highlighted.

It will be appreciated that the same thing can be said in more than one way. Hence, alternative language and synonyms can be used for any one or more of the terms discussed herein. Nor is any special significance to be placed upon whether or not a term is elaborated or discussed herein. Synonyms for certain terms can also be provided herein. A recital of one or more synonyms does not exclude the use of other synonyms, for example. The use of examples anywhere in this specification including examples of any terms discussed herein is illustrative only and is not intended to further limit the scope and meaning of the disclosure or of any exemplified term. Likewise, the disclosure is not limited to various embodiments given in this specification.

As used herein, the singular forms "a," "an" and "the" include plural referents unless the context clearly dictates otherwise. Thus, for example, reference to a "capsule" includes aspects having two or more capsules unless the context clearly indicates otherwise.

Ranges can be expressed herein as from "about" one particular value, and/or to "about" another particular value. "About" as used herein means plus or minus 5% of a numerical value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

As used herein, a "capsule" refers to a pharmaceutical device having at least one body and at least one cap that can be coupled together to define at least one chamber for a dosage. In certain example embodiments, the capsule includes a liquid fill, such as a suspension or semisolid, a powder fill and/or a granular fill which is positioned in the chamber to form a single, hermitically sealed dosage form. As one skilled in the art will appreciate, any portion of the capsule can be composed of gelatin, a plasticizer, and water, and can also include other ingredients such as preservatives, coloring, flavorings, opacifying agents, sweetening agents, acids, salts, medicaments, or other agents to achieve a desired dosage effect.

As used herein, a "subject" refers to a vertebrate. The vertebrate may be a mammal, for example, a human. The subject may be a human patient. A subject may be a patient suffering from or suspected of suffering from a disease or condition and may be in need of treatment or diagnosis or may be in need of monitoring for the progression of the disease or condition. The patient may also be on a treatment therapy that needs to be monitored for efficacy.

As used herein, "pharmaceutically acceptable salts" refer to derivatives of a given compound, such as an active ingredient, wherein the therapeutic compound is modified by making acid or base salts thereof. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. For acidic compounds, the salt may include an amine-based (primary, secondary, tertiary or quaternary amine) counter ion, an alkali metal cation, or a metal cation. Lists of suitable salts are found in texts such as Remington's Pharmaceutical Sciences, 18th Ed. (Alfonso R. Gennaro, ed.; Mack Publishing Company, Easton, Pa., 1990); Remington: the Science and Practice of Pharmacy 19th Ed.(Lippincott, Williams & Wilkins, 1995); Handbook of Pharmaceutical Excipients, 3rd Ed. (Arthur H. Kibbe, ed.; Amer. Pharmaceutical Assoc., 1999); the Pharmaceutical Codex: Principles and Practice of Pharmaceutics 12th Ed. (Walter Lund ed.; Pharmaceutical Press, London, 1994); The United States Pharmacopeia: The National Formulary (United States Pharmacopeial Convention); and Goodman and Gilman's: the Pharmacological Basis of Therapeutics (Louis S. Goodman and Lee E. Limbird, eds.; McGraw Hill, 1992), the disclosures of which are hereby incorporated by reference in their entirety. As used herein, an active ingredient can include a pharmaceutically acceptable salt of the active ingredient.

As used herein, a "probiotic" generally means live bacteria (also called microflora or microorganisms) that confer a beneficial effect when an effective amount is introduced into the intestinal tract of a mammal.

"Prebiotic" means any substance that can be consumed by a relevant probiotic, or that otherwise assists in keeping the relevant probiotic alive or stimulates its growth, and includes mucopolysaccharides, oligosaccharides, polysaccharides, amino acids, vitamins, nutrient precursors and proteins. "Compliment" or "complimentary" with respect to a prebiotic means that the prebiotic is consumed by, or otherwise assists in keeping alive or stimulates the growth of, a relevant probiotic.

EXAMPLE EMBODIMENTS

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily, are references to the same embodiment. And, such references mean at least one of the embodiments.

Further, reference to an "embodiment" or "example embodiment" means that a particular feature, structure, or characteristic described in connection with the embodiment is included in at least one embodiment of the disclosure. Similarly, the appearance of the phrase "in certain embodiments" in various places herein are not necessarily all referring to the same embodiment, nor are separate or alternative embodiments mutually exclusive of other embodiments. Moreover, various features are described which can be exhibited by some embodiments and not by others. Similarly, various requirements are described which can be requirements for some embodiments but not other embodiments.

Dual Dosage Release Capsule

Figure 2:
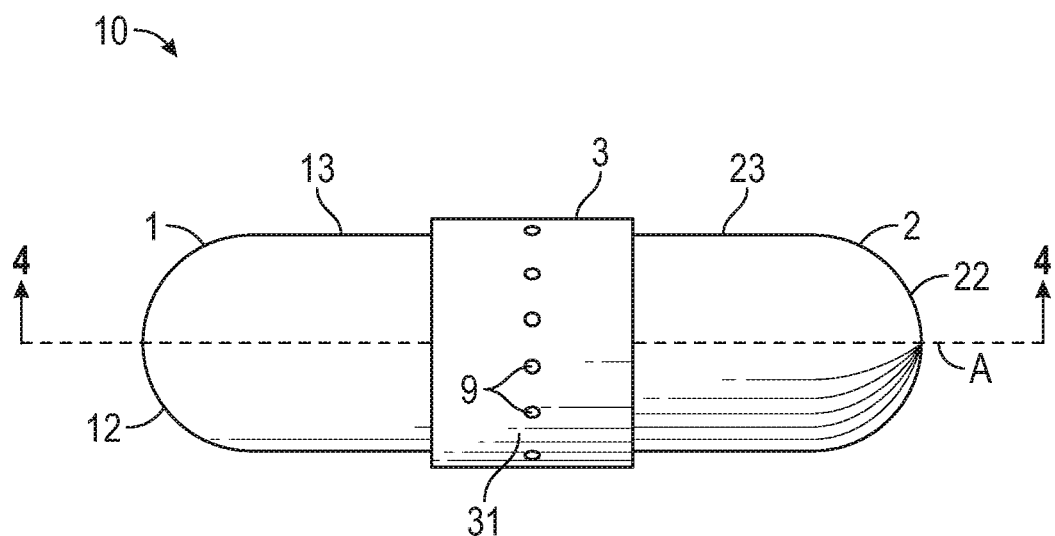
FIG. 2 is a side view of a dual release dosage form capsule having a plurality of apertures in the band, in accordance with certain example embodiments.
Figure 3:
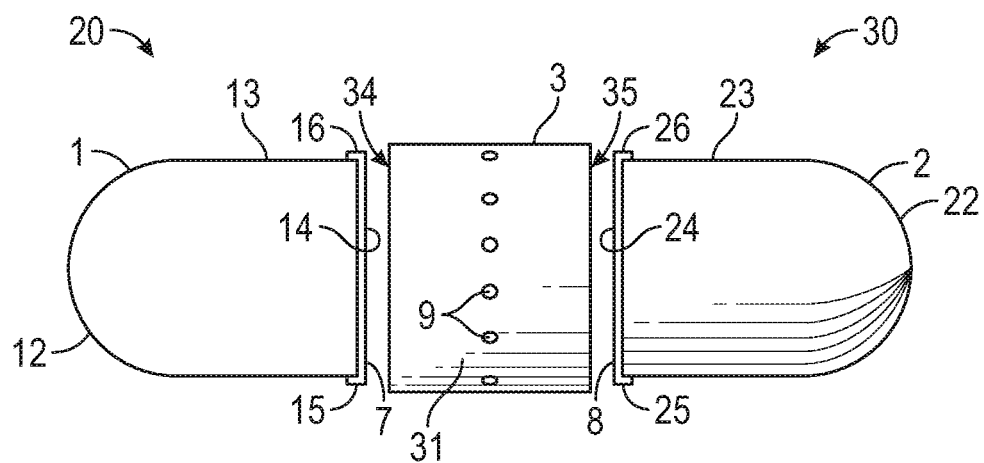
FIG. 3 is an exploded view of the capsule of FIG. 2, in accordance with certain example embodiments.

Turning to the drawings, FIGS. 1-3 are illustrations depicting example dual dosage form capsules 10, in accordance with certain example embodiments, with or without a plurality of apertures in the band 3. As shown, the capsule can include a first shell body 1 and an opposed second shell body 2. A first cap 7 can be sized and configured to enclose a first open end 11 of the first shell body, and a second cap 8 can be sized and configured to enclose a second open end 21 of the second shell body. A band 3 can be coupled to the first shell body 1 and the second shell body 2 to form the dual dosage form capsule 10.

The first shell body 1 includes the first open end 11, a first closed end 12 and a first sidewall 13 extending therebetween. The first sidewall and the first closed end cooperate to define a first chamber 5, the first chamber being in fluid communication with the atmosphere via the first open end. That is, the first chamber 5 of the first shell body can be accessible through the first open end 11. In another example embodiment, at least portions of the first closed end 12 and/or the first sidewall 13 can be arcuate in shape. For example, at least a portion of the first sidewall can be substantially cylindrical in shape, such that the first open end 11 is substantially circular in cross section having a first end diameter. Of course, other shapes of the first open end, the first closed end, and the first sidewall are contemplated.

Figure 4:
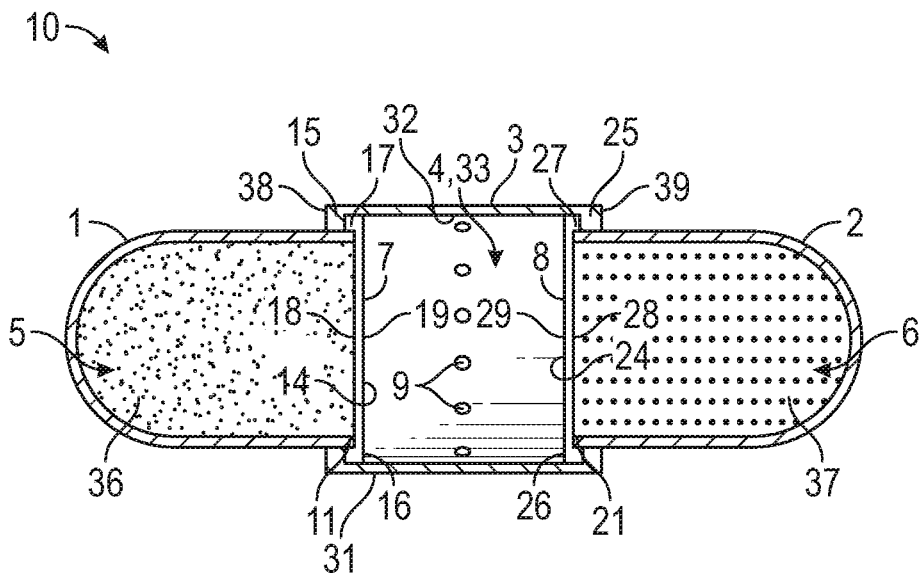
FIG. 4 is cross-sectional view of an example capsule, illustrating the profile taken through the line 4-4 as shown in FIG. 2, in accordance with certain example embodiments.

Referring to FIGS. 3 and 4, the first cap 7 is sized and configured to close the first open end 11 of the first shell body 1. In certain example embodiments, the first cap 7 can include a first cover 14 having a similar size and shape as the first open end. Optionally, the first cover 14 can have a slightly larger size and/or shape than the first open end 11. For example, if the first open end is substantially circular having a first end diameter, the first cap 7 can be substantially circular having a first cover diameter that is greater than or equal to the first end diameter. In another example embodiment, the first cover 14 can have an inner surface 18 configured to face the first chamber 5 when assembled and an opposed outer surface 19 configured to face away from the first chamber when assembled.

A first lip 15 extends from the distal edge 16 of the first cover 14. In one example embodiment, at least a portion of the first lip 15 can extend from the distal edge 16 of the first cover 14 at a substantially right angle relative to the first cover. Optionally, at least a portion of the first lip 15 can extend from the distal edge 16 of the first cover 14 at an acute angle relative to the first cover. In use, and described more fully below, at least a portion of the first cover 14 and/or the first lip can engage a distal edge 17 of the first sidewall 13 to seal a first fill material 36 (FIG. 4) in the first chamber 5 and form a first capsule member 20. For example, at least a portion of the first cover 14 and/or the first lip can frictionally engage the distal edge 17 of the first sidewall 13 to seal the first chamber and form the first capsule member. In another example embodiment, a laser or other heat source can be directed to at least a portion of the first cover 14 and/or the first lip to seal the first chamber 5 and form the first capsule member 20.

The second shell body 2 includes the second open end 21, a second closed end 22, and a second sidewall 23 extending therebetween. The second sidewall and the second closed end can cooperate to define a second chamber 6, the second chamber being in fluid communication with the atmosphere via the second open end. That is, the second chamber of the second shell body can be accessible through the second open end 21. In certain example embodiments, at least portions of the second closed end 22 and the second sidewall 23 can be arcuate in shape. For example, at least a portion of the second sidewall can be substantially cylindrical in shape, such that the second open end 21 is substantially circular in cross section having a second end diameter. Of course, other shapes of the second open end, the second closed end and the second sidewall are contemplated. In a further embodiment, the second end diameter can be less than, substantially equal to, or greater than the first end diameter.

The second cap 8 can be sized and configured to enclose the second open end 21 of the second shell body 2. In one example embodiment, the second cap 8 can include a second cover 24 having a similar size and shape as the second open end 21. Optionally, the second cover 24 can have a slightly larger size and/or shape than the second open end 21. For example, if the second open end 21 is substantially circular having a second end diameter, the second cap 8 can be substantially circular having a second cover diameter that is greater than or equal to the second end diameter. In another example embodiment, the second cover diameter can be less than, substantially equal to, or greater than the first cover diameter. In a further example embodiment, the second cover 24 can have an inner surface 28 configured to face the second chamber 6 when assembled and an opposed outer surface 29 configured to face away from the second chamber when assembled.

A second lip 25 extends from a distal edge 26 of the second cover 24. For example, at least a portion of the second lip can extend from the distal edge of the second cover at a substantially right angle relative to the second cover 24. Optionally, at least a portion of the second lip 25 can extend from the distal edge of the second cover at an acute angle relative to the second cover 24. In use, described more fully below, at least a portion of the second cover and/or the second lip can engage a distal edge 27 of the second sidewall 23 to seal a second fill material 37 in the second chamber 6 and form a second capsule member 30. For example, at least a portion of the second cover 24 and/or the second lip 25 can frictionally engage the distal edge 27 of the second sidewall 23 to seal the chamber and form the second capsule member. In another example embodiment, a laser or other heat source can be directed to at least a portion of the second cover 24 and/or the second lip to seal the second chamber 6 and form the second capsule member 30.

Figure 7:
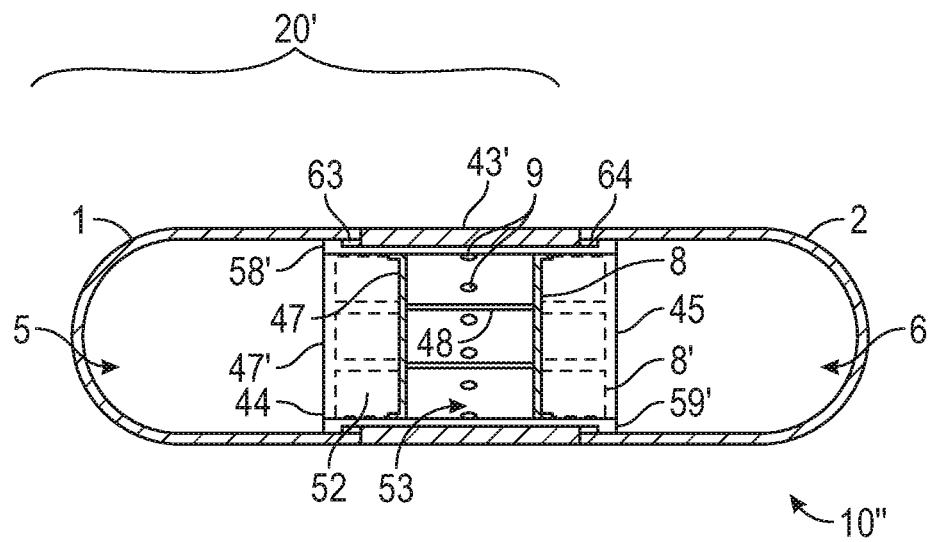
FIG. 7 is a cross-sectional assembled view of an inside fit for the ends of a band that is similar to the band of FIG. 5A.

As shown in FIGS. 1-4, the band 3 is an endless annular band including an outer surface 31 having an outer diameter and an inner surface 32 (labeled in FIG. 4) having an inner diameter. Thus, a passage 33 having a first entry port 34 and an opposed second entry port 35 can be defined in and extend through the annular band. In all aspects, the inner diameter of the band 3 can be substantially equal to, slightly greater than, or slightly smaller than at least one of the first end diameter of the first shell body 1, the first cover diameter of the first cap 7, the second end diameter of the second shell body 2, and the second cover diameter of the second cap 8 to provide for an outside fit as shown in FIGS. 1-6 and 8 or an inside fit as shown in FIG. 7.

The band in any and/or all of these embodiments includes a snap-fit or click-fit feature to connect the band to the first shell body 1 and second shell body 2, but it is not required to have this feature. In FIG. 4, the band 3 has a flange 38 at the periphery of the first end port 34 that extends radially inward toward the first shell body 1 and snaps or clicks over the end of the first lip 15 of cap 7. Likewise, the band 3 has a flange 39 at the periphery of the second end port 35 that extends radially inward toward the second shell body 2 and snaps or clicks over the end of the first lip 25 of cap 8. In FIG. 5A-6 each of the first shell body and second shell body 1, 2 have an exterior ridge 61, 62 at the open ends thereof over which the flanges 58, 59 of band 43 snap-fit or click-fit. And, in FIG. 7 each of the first shell body and the second shell body 1, 2 have an interior ridge 63, 64 at the open ends thereof over which flanges 58', 59' of the band 43' snap-fit or click-fit.

Figure 8:
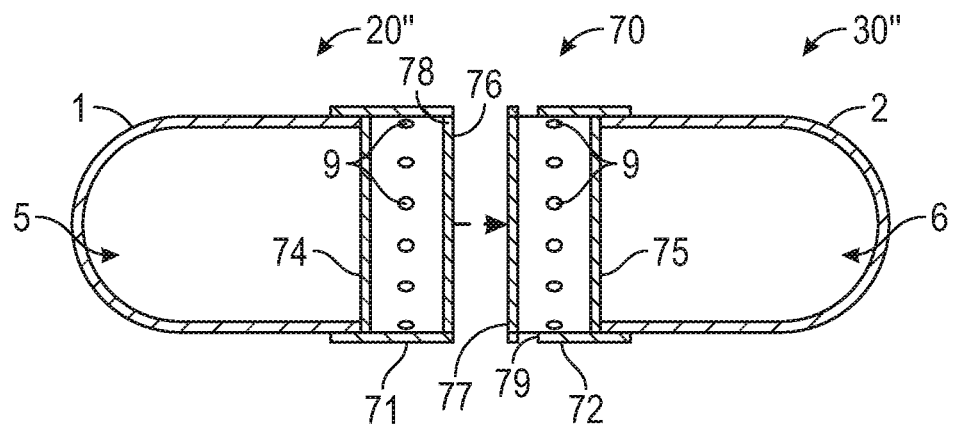
FIG. 8 is a cross-sectional partial assembled view of a capsule having lids integral with annular band portions that are mateable to one another to form the band.

In any and all embodiments, at least one aperture 9, but preferably a plurality of apertures 9, can be defined in a portion of the band that extends from the outer surface 31 of the band to the inner surface 32, thus allowing communication between the environment surrounding the outer surface 31 of the band 3 and the environment inside passage 33 of the band 3. In one embodiment, when a plurality of apertures 9 are present, the apertures are spaced equidistant apart around 9 the band in a plane transverse to the longitudinal axis along line 4-4 of FIG. 2, thereby forming a perforated ring in the band. In another embodiment, the plurality of apertures is positioned as two separate groups of apertures in two different planes transverse to the longitudinal axis as shown in FIG. 8. While the illustration in FIG. 8 has the apertures aligned with one another in the two planes, the apertures, may be offset relative to one another.

Referring now to FIGS. 5A-7, alternate embodiments for the band are illustrated in which one of the covers for the first or second shell body 1, 2 is built into the band, i.e., is integral therewith to reduce the number of parts for the assembly process. Here the band 43 is an endless annular band having an outer surface 51 having an outer diameter and an inner surface 52 (labeled in FIG. 5A) having an inner diameter. A cover 47 spanning the inner diameter to sealingly close one of the first or second shell bodies 1, 2, is integral within the band 43 at a position more proximate a first end 44 thereof than a second end 45 thereof. In the embodiment of FIGS. 5A-6, the first end 44 defines a first entry port 54 and the second end 45 defines an opposed second entry port 55 for ultimate receipt of the open ends of the first and second shell bodies 1, 2, respectively. The inner surface 52 of band 43 includes a feature, such as ribs 48 or an annular shoulder (not shown), to define a seat for receipt of a cap 8. Cap 8 may be received in band 43 alone and fixedly, sealingly connected thereto by any suitable methods known or hereinafter developed as shown in FIG. 5B, or cap 8 may be sealing connected to the second shell body 2, which is then received into the band 43 as a unit as illustrated with dashed lines in FIG. 5A.

A plurality of apertures 9, as described above, are present in the band 43 at a position between the cover 47 and the cap 8. Further, in the assembled state of FIGS. 5B and 6, an internal chamber 53 is defined between the cover 47 and the cap 8 and is in fluid communication with the exterior environment through the plurality of apertures 9.

Referring now to FIG. 7, when the band is for an inside fit, it is designated 43' and the cover 47 may be positioned within the band or alternately, the cover may be in the position of 47' at and closing the first end 44 of the band shown with dashed lines in the drawing. Likewise, cap 8 may be positioned within the band or it may be in the position 8' at and closing the second end 45 of the band as shown with dashed lines in the drawing. The inner surface 52 of band 43' includes a feature, such as ribs 48 or an annular shoulder (not shown), to define a seat for receipt of cap 8. Hereto, a plurality of apertures 9, as described above, are present in the band 43' at a position between the cover 47 and the cap 8 or cover 47' and cap 8'. Further, an internal chamber 53 is defined between the cover 47 and the cap 8 or cover 47' and cap 8' and is in fluid communication with the exterior environment through the plurality of apertures 9.

Referring now to FIG. 8, the band may have a two-part construction 70 where each annular band portion 71, 72 has a cover 74, 75, respectively, for sealingly closing a shell body integral therewith. The first annular band portion 71 and the second annular band portion 72 each have an open end 76, 77 opposite the cover 74, 75 therein and the open ends 76, 77 are connectable to one another to form a band connecting the two halves of the capsule into a complete capsule unit. The connection between the first and second annular band potions 71, 72 is illustrated as snap-fit or click-fit feature shown as an annular ridge 78 in the inside of the shell body 1 and defining the open end 76 and an annular groove 79 for receiving the annular ridge 78 in the exterior surface of the second annular band 72. The reverse configuration is also possible. Here, the first annular band portion 71 and/or the second annular band portion 72 includes a plurality of apertures 9 therethrough radially oriented relative to a longitudinal axis of the capsule, thereby placing an internal chamber formed between the covers 74, 75 in the assembled state in fluid communication with the environment outside the capsule.

Referring back to FIG. 3, to form the first and second capsule members 20, 30, a first predetermined amount of a first fill material 36 can be inserted through the first open end 11 of the first shell body 1 and into the first chamber 5. The first cap 7 can be positioned over the first open end and at least a portion of the first cap 7 can be coupled to the first shell body to the form the first capsule member 20 having the first fill material 36 sealed inside the first chamber. For example, the first cap 7 can be positioned over the first open end 11 and at least a portion of the first cap 7 can be heat sealed to the first shell body 1 to the form the first capsule member 20 having the first fill material 36 sealed inside the first chamber 5. Similarly, a second predetermined amount of a second fill material 37 can be inserted through the second open end 21 of the second shell body 2 and into the second chamber 6. The second cap 8 can be positioned over the second open end and at least a portion of the second cap can be coupled to the second shell body to form the second capsule member 30 having the second fill material sealed inside the second chamber. For example, the second cap 8 can be positioned over the second open end 21 and at least a portion of the second cap can be heat sealed to the second shell body 2 to form the second capsule member 30 having the second fill material 37 sealed inside the second chamber 6.

To form the capsule 10 of FIG. 1 or FIG. 2, the band 3 couples the first capsule member 20 to the second capsule member 30. As described more fully below, at least a portion of the first open end 11 (sealed with the first cap 14) of the first shell body 1 is inserted through the first entry port 34 and into the passage 33 of the band. In one example embodiment, the first shell body can be positioned so that it passes through the first entry port but does not extend to the second entry port 35. That is, at least a portion of the first shell body 1 can be positioned in the passage 33 without extending all the way through the passage from the first entry port 34 to the second entry port 35. Similarly, at least a portion of the second open end 21 (sealed with the second cap 24) of the second shell body 2 can be inserted through the second entry port 35 and into the passage 33 of the band. In certain example embodiments, the second shell body can be positioned so that it passes through the second entry port 35 but does not extend to the first entry port 34. That is, at least a portion of the second shell body 2 can be positioned in the passage 33 without extending all the way through the passage from the second entry port 35 to the first entry port 34.

In the passage 33 of the band 3, the first capsule member 20 can be spaced from the second capsule member 30 a predetermined distance. The predetermined distance is a distance greater than zero such that a third chamber 4 or 33 (FIG. 4) is defined by the first capsule member 20, the second capsule member 30 and the inner surface 32 of the band 3. In such example embodiments, the apertures 9 defined in the band can place the third chamber 4 in sealed fluid communication with the atmosphere/environment outside the capsule 10.

To form the capsule 10' of FIG. 6 or capsule 10" of FIG. 7, the band can be coupled to the shell bodies 1 and 2 in various steps. In one variation, according to FIG. 5A, the band 43 is mated to the open end of the first shell body 1 as an outside fit (FIG. 6) after being filled with fill material. Cap 8 is sealingly connected to the open end of the second shell body 2 after being filled with fill material to form a second capsule member 30. This second capsule member 30 is received in the open end 55 of the band 43 to form capsule 10'. In another variation according to FIGS. 5A and 5B, a cap 8 is securely seated within the band 43. The first shell body 1 is filled with fill material and the open end thereof is sealingly received within the band 43 to form a first capsule unit. The second shell body 2 is filled with fill material and the open end of the first capsule unit formed by the band 43 is seated over the open end of the second shell body 2 to sealingly close the second shell body 2 and form the capsule 10'. In another variation, according to FIG. 7, a cap 8 or 8' is securely seated within band 43'. Then, the first shell body 1 is filled with fill material and the open end thereof sealing receives a first end of the band 43' therein to form a first capsule unit. The second shell body 2 is filled with fill material and the open end thereof sealingly receives the second end of the band 43' therein to form capsule 10".

To form a capsule from the first capsule member 20" and the second capsule member 30" of FIG. 8, the first shell body 1 is filled with fill material and is sealingly mated to the first annular band portion 71 with either an outside fit as shown or an inside fit as illustrated in FIG. 7. The second shell body 2 is filled with fill material and is sealingly mated to the second annular band portion 72 with either an outside fit as shown or an inside fit as illustrated in FIG. 7. Then, the first and second capsule members 20" and 30" are mated together using the open ends 76, 77 of first and second annular band portions 71, 72, thereby forming a complete capsule.

In all aspects, once the shell bodies, caps, bands, capsule members, etc. are in the desired positions to form a capsule, the band can be sealed to the respective parts/members using known or hereinafter developed techniques. For example, the band can be sealed with heat, such as a laser or an oven, with adhesives. In another example, the band can be friction fit to the shell bodies and/or have the snap-fit or click-fit features described above.

In any of the embodiments disclosed herein, the first shell body 1, cap 7, band 43, band 43', and first annular band portion 71 can be formed from different materials than the second shell body 2, cap 8, cap 8', and second annular band portion 72, so that these respective components dissolve at different rates. As an illustrative example the caps 7 and 8 are discussed further below. These examples are equally applicable to any other combination of respective shell bodies, bands and caps and annular band portions. The first cap 7 of the first capsule member 20 can be formed from a different material than the second cap 8 of the second capsule member 30 such that the caps dissolve at different rates, and thus, the contents of the respective first and second chambers 5, 6 can be released at different times when the capsule is ingested. As such, the fill material of the first and second chambers 5, 6 can be released sequentially. For example, the first fill material 36 can be released near the time of ingestion, while the second fill material 37 can be released minutes our hours later, such as 1, 2, 3, 4, 5, or 6 hours after release of the first fill material 36. Allowing portions of the first capsule member 20 and the second capsule member 30 to be dissolved at different rates allows a dual timing release so that the first fill material 36 positioned in the first chamber 5 can be released from the first chamber at a different time than the second fill material 37 positioned in the second chamber 6.

In any of the embodiments disclosed herein, the first shell body 1, cap 7, band 43, band 43', and first annular band portion 71 can be formed from the same or different materials than the second shell body 2, cap 8, cap 8', and second annular band portion 72, so that the capsule members dissolve at approximately the same rate. As an illustrative example the caps 7 and 8 are discussed further below. These examples are equally applicable to any other combination of respective shell bodies, bands and caps and annular band portions. For example, the first cap 7 of the first capsule member 20 can be formed from the same material as the second cap 8 of the second capsule member 30 such that the caps dissolve at substantially the same rate, and thus, the contents of the respective first and second chambers 5, 6 can be released at substantially the same time. Allowing portions of the first capsule member 20 and the second capsule member 30 to be dissolved at substantially the same time allows a substantially simultaneous release of at least two fill materials. For example, if two pharmaceutical agents undesirably interact during shelf life, such as when mixed, one pharmaceutical agent can be inserted into the first chamber 5 of the first capsule member 20, and a second pharmaceutical agent can be inserted into the second chamber 6 of the second capsule member. In such example embodiments, the first and second pharmaceutical agents would not interact with each other until the substantially simultaneous release. In other example embodiments, the first and second materials 36, 37 may be separated as described herein to both prevent any undesirable interaction between the fill materials and to permit sequential release of the first and second fill materials as described herein.

In use, the at least one aperture 9 in the band 3 can permit fluid to enter the third chamber 4, 33 such as digestive fluid when the dual release dosage form capsule is swallowed and enters the digestive tract. The digestive fluid can then contact the caps 7, 8, thereby dissolving the caps as described herein. In certain example embodiments, once a cap is at least partially digested, the fill material within the capsule member associated with at least partially dissolved cap can move into the third chamber 4 and then out of the dosage form through the one or more apertures 9 (and hence into the environment surrounding the dual release dosage form). Additionally or alternatively, in use the fluid entering the third chamber 4 can cause the band 3 to completely or partially fall off of the capsule members 20, 30 so that the first cover 14 of the first capsule member and the second cover 24 of the second capsule member are fully or partially exposed. In such example embodiments, the caps can then be dissolved when exposed to the fluid, such as digestive fluid. The capsule members can then release their fill material in a substantially simultaneously manner, or in a dual timed manner, as described herein.

Additionally or alternatively, in use the fluid entering the third chamber 4, 33 causes the band to at least partially dissolve so that the first cover of the first capsule member 20 and the second cover of the second capsule member 30 are at least partially exposed. The exposed covers of the capsule members can then be dissolved, such as via digestive fluid. If the first cap 7 is formed from a different material than the second cap 8 such that the caps dissolve at different rates, the contents of the respective first and second chambers 5, 6 can be released at different times. If the first cap 7 is formed from the same material as the second cap 8 such that the caps dissolve at substantially the same rate, the contents of the respective first and second chambers 5, 6 can be released at substantially the same time.

When a rapidly dissolving portion of the dual release dosage form capsule is desired, such as a rapidly dissolving band and/or a cap (7 or 8), the rapidly dissolving portion can be made from an inert and non-toxic composition that is at least partially, and preferably substantially completely, soluble and/or erodible in an environment of use. For example, the rapidly dissolving portion will be soluble and/or erodible in aqueous environments such as, for example, the buccal cavity and/or upper GI tract, e.g., the stomach, duodenum, jejunum or upper small intestines. Exemplary materials are disclosed in U.S. Pat. Nos. 4,576,604 and 4,673,405, and the text Pharmaceutical Dosage Forms: Tablets Volume I, Second Edition. (A. Lieberman. ed. 1989, Marcel Dekker, Inc.), the relevant disclosures of which are hereby incorporated by reference in their entirety. In certain example embodiments, the rapidly dissolving portion of the dual release dosage form capsule 10 will be substantially soluble (or erodible) in saliva, gastric juices, or acidic fluids.

According to the U.S. Department of Health and Human Services Food and Drug Administration Center for Drug Evaluation and Research (CDER), an immediate release drug product is considered rapidly dissolving when a mean of 85 percent or more of the labeled amount of the drug substance dissolves within 30 minutes, using United States Pharmacopeia (USP) Apparatus 1 at 100 rpm or Apparatus 2 at 50 rpm (or at 75 rpm when appropriately justified (see section III.C.) in a volume of 500 mL or less (or 900 mL when appropriately justified) in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes. Further, an immediate release product is considered very rapidly dissolving when a mean of 85 percent or more of the labeled amount of the drug substance dissolves within 15 minutes, using the above-mentioned conditions.

When a slowly dissolving portion of the dual release dosage form capsule is desired, such as a slowly dissolving cap (7 or 8), the slowly dissolving portion can be made from several known digestion-resistant polymer compositions, including those conventionally used for enteric coating. Such cap formulations, for example, provide a delayed and sustained release of fill material and can include materials that are soluble or erodible in intestinal juices, substantially pH neutral or basic fluids but for the most part insoluble in gastric juices or acidic fluids. A wide variety of polymeric materials are known to possess these various solubility properties. Such polymeric materials include, for example, cellulose acetate phthalate (CAP), cellulose acetate trimelletate (CAT), poly(vinyl acetate) phthalate (PVAP), hydroxypropyl methylcellulose phthalate (HP), poly(methacrylate ethyl acrylate) (1:1) copolymer (MA-EA), poly (methacrylate methyl methacrylate) (1:1) copolymer (MA-MMA), poly(methacrylate methyl methacrylate) (1:2) copolymer, Eudragit L-30-D™ (MA-EA, 1:1), Eudragit™ L-100-55™ (MA-EA, 1:1), hydroxypropyl methylcellulose acetate succinate (HPMCAS), Coateric™ (PVAP), Aquateric™ (CAP), AQUACOAT™ (HPMCAS) and combinations thereof. The slow release cap, for example, can also include dissolution aids, stability modifiers, and bioabsorption enhancers.

In certain example embodiments, the slowly dissolving portion of the dual release dosage form capsule, such as the slowly dissolving cap, includes hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA: MMA: MA synthesized in the presence of N,N'-bis(methacryloyloxyethyloxycarbonylamino)-azobenzene, azopolymers, enteric coated timed release system components (Time Clock® from Pharmaceutical Profiles, Ltd., UK) and/or calcium pectinate. In certain example embodiments, a poly (vinylpyrrolidone)-vinyl acetate copolymer (e.g., material supplied by BASF under its Kollidon VA64™) mixed with magnesium may be used, such as stearate and other similar excipients. Povidone, which is supplied by BASF under its Kollidon K 30™, and hydroxypropyl methylcellulose, which is supplied by Dow under its Methocel E15™, can also be used in certain example embodiments.

In certain example embodiments, the slowly dissolving portion of the dual release dosage form capsule, such as the slowly dissolving cap, can include one or more agents that do not disintegrate (or change their structural integrity) in the stomach and during the period that the capsule resides in the stomach. Representative materials that keep their integrity in the stomach can include (a) keratin, keratin sandaractolu, salol (phenyl salicylate), salol beta-naphthylbenzoate and acetotannin, salol with balsam of Peru, salol with tolu, salol with gum mastic, salol and stearic acid, and salol and shellac; (b) formalized protein, formalized gelatin, and formalized cross-linked gelatin and exchange resins; (c) myristic acid-hydrogenated castor oil-cholesterol, stearic acid-mutton tallow, stearic acid-balsam of tolu, and stearic acid-castor oil; (d) shellac, ammoniated shellac, ammoniated shellac-salol, shellac-wool fat, shellac-acetyl alcohol, shellac-stearic acid-balsam of tolu, and shellac n-butyl stearate; (e) abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methyl methacrylate 50:50 copolymer of 135,000 molecular weight, methacrylic acid-methylmethacrylate-30:70-copolymer of 135,000 mol. wt., methacrylic acid-dimethylaminoethylmethacrylate-ethyl acrylate of 750,000 mol. wt., methacrylic acid-methyl methacrylate-ethyl acrylate of 1,000,000 mol. wt., and ethyl acrylate-methyl methacrylate-ethyl acrylate of 550,000 mol. wt; and, (g) an enteric composition including cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl includes from 1 to 7 straight and branched alkyl groups, aryl phthalates, and other materials known to one or ordinary skill in the art.

As those skilled in the art will appreciate based on this disclosure, a variety of fill materials can be used with the dual release dosage form as described herein, the fill materials including various active ingredients and non-active ingredients. In certain example embodiments, the first fill material 36 positioned in the first shell body 1 can include the same or substantially the same active ingredient as the second fill material 37 positioned in the second shell body 2. Such embodiments are particularly useful to extend the release of a given drug. For example, the first fill material 36 can include a pharmaceutical agent that can be quickly released, thereby providing an initial dosage of the pharmaceutical when the dual release dosage form is exposed to fluids such as digestive fluids. The second fill material 37, in such embodiments, can include the same pharmaceutical agent, the second half of the capsule being configured however to release the pharmaceutical agent after the initial dosage as described herein. Hence, the overall release of the same pharmaceutical agent is extended. For example, the overall release of the pharmaceutical agent can be extended by about 30, 40, 50, 60, 70, 80, 90, 100, 110 minutes or more as compared to a single dosage of the pharmaceutical agent. In certain example embodiments, the release is extended by about 2, 3, 4, 5, 6, 7, 8, 9, or 10 hours.

Alternatively, in certain example embodiments the active ingredients or pharmaceutically acceptable salts thereof of the first fill material 36 can be different than the active ingredients or pharmaceutically acceptable salts thereof of the second fill material 37. The fill material positioned in the capsules, such as the first fill material 36, the second fill material 37 and any other number of fill materials, can be any material known in the art, such as those commonly included in capsules. For example, the first fill material 36 can include ibuprofen as the active ingredient and the first cap 7 is formulated to rapidly release the ibuprofen. In the same dual release dosage capsule, for example, the second fill material 37 can include acetaminophen as the active ingredient and the cap 8 is formulated and/or configured to slowly release the acetaminophen as described herein. Hence, ingestion of such a dosage form results in an initial release of ibuprofen that is followed by a later (delayed) release of acetaminophen. Such a dual release, for example, provides two fever reducers and pain relievers in the same dosage form, thus dispensing with the common need to separately administer ibuprofen and acetaminophen at different times.

While the above example relates to ibuprofen and acetaminophen, the fill materials 36, 37 can include any active ingredients or combination of active ingredients, including pharmaceutical agents and/or nutraceuticals. For example, if the desired effect of the capsule is targeted toward urinary tract health, an example active ingredient of cranberry, such as cranberry extract, can be included as the active ingredient of the fill material. If the desired effect is heart health, the active ingredient can include an emulsified fatty acid, such as an emulsified omega-3 or omega-7 fatty acid. In certain example embodiments, the active ingredient is palmitoleic acid. In certain example embodiments, the active ingredient is Omega-9. In certain example embodiments, the active ingredient is hyaluronic acid. The active ingredient can also include any medicaments, vitamins, minerals, fruits, herbals, and/or other materials or combinations thereof understood by those skilled in the art to support a desired effect. For example, if the effect desired is mineral supplementation, exemplary active ingredients can be calcium, magnesium and Vitamin D. In certain example embodiments, the active ingredient can include krill oil, salmon oil, and/or flax seed oil, such as highly purified flax seed oil. In certain example embodiments, mixtures of active ingredients can be included in the fill material, such that a given dual release dosage capsule may include 1, 2, 3, 4, 5, 6, or 7 or more active ingredients.

In addition to active ingredients, the fill materials described herein can include a variety of other non-active components, such as non-active components that are typically included in pharmaceutical and/or nutraceutical formulations. For example, the fill material can include a liquid carrier and active ingredient, the active ingredient being suspended within the liquid carrier. In certain example embodiments, the liquid carrier is a water-immiscible liquid, such as a vegetable and/or aromatic oil, an aromatic and aliphatic and aliphatic hydrocarbon, a chlorinated hydrocarbon, an ether, an ester, high molecular weight organic acid and/or alcohol, or lower molecular weight polyalkylene glycol. Other embodiments can contain water-miscible liquid carriers as well. In certain example embodiments, the active ingredients of the fill material may be formulated as pharmaceutically acceptable salts.

In certain example embodiments—and distinct from the dual time release achieved via the structural design of the dual release dosage form capsules described herein—the active ingredient or ingredients in one or both fill materials 36, 37 can be formulated to modify the release rate of the active ingredient. For example, the active ingredient can be embedded in a matrix of one or more insoluble, such that the dissolving active ingredient must find its way out through the holes in the matrix (thus slowing the release). In certain example embodiments, the matrix can physically swell to form a gel, thus allowing the active ingredient to exit through the gel's outer surface. In certain example embodiments, the active ingredient is coated or layered with a slow-release material. In other example embodiments, the microencapsulation can be used to modify and further control the release of the active ingredient. In certain example embodiments, the slow-release formulation of the active ingredient may be an extended-release dosage that includes a sustained-release and/or controlled-release dosage, as known in the art.

Such slow-release formulations, which are generally known in the art, can be used in conjunction with the dual release capsules described herein to further delay the release of active ingredient from the fill materials. For example, the first fill material 36 can be a rapid release material that, upon contact with gastric fluids, quickly releases the active ingredient into the environment surrounding the dosage form. The cap 8 may be formulated to slowly dissolve, thereby delaying the release of the second fill material 37 relative to the first fill material 36 as described herein. Yet further, the second fill material 27 can include binders, excipients, matrices and/or other components associated with the active ingredient that function to slow the dissolve-time, for example, of the active ingredient of the second fill material 37. Hence, delay in release of the active ingredient from the second fill material 37 can result from both the cap 8 that is formulated to slowly dissolve and secondarily the slow-release formulation of the active ingredient in the second fill material 37. In certain example embodiments, the slow-release formulation of the active ingredient may be an extended-release dosage that includes a sustained-release and/or controlled-release dosage, as known in the art.

As those skilled in the art will appreciate, many active ingredients are beneficial when consumed together. For example, two or more active ingredients may act synergistically when consumed together. However, not all active ingredients or fill materials can be mixed together within the same dosage form, as certain active ingredients and/or fill materials can be incompatible with each other. For example, chemical reactions may occur that destabilize the mixed active ingredients or that result in gas evolution. Or, the pH needed to dissolve or suspend two active ingredients may be different, thus preventing the two active ingredients from being mixed within the same dosage form.

In certain example embodiments, provided is a dual dosage form capsule in which the fill materials having different pH values. For example, the first fill material has a pH of about 2, 3, 4, 5, or 6, whereas the second fill material has a pH of about 7, 8, 9, or 10. Such embodiments are particularly useful when different pH values are required to dissolve, suspend, stabilize, or otherwise mix different active ingredients. For example, the first fill material can include an olive leaf extract, such as oleuropein, which is typically adjusted to a pH of around 6-7. The second fill material can include, for example, vitamin C and/or elderberry juice at a pH of around 2-5. Such embodiments, for example, can prevent destabilization of the oleuropein that can occur if the pH of the oleuropein is reduced to around 3.5 pH.

In certain example embodiments, provided is a dual dosage form capsule that includes one or more antioxidants and a fatty acid as the fill materials. For example, the first fill material can include reduced glutathione (GSH) while the second fill material can include an omega fatty acid, such omega-3, 5, 6, 7, 9. As those skilled in the art will appreciate, GSH is a metal chelator that is used in detoxification scenarios. GSH, however, is not stable when subjected to long-term storage in solution, where metal cations are present in the solution. The thiol group on the glutathione undergoes gradual oxidation to a disulfide, a reaction that is catalyzed by the presence of molecular oxygen or of certain metal ions, such as $Fe^{+3}$ or $Cu^{+2}$. As the reaction proceeds, there is a gradual reduction in the efficacy of the reduced glutathione solution, thus reducing its antioxidant ability. Fatty acid compositions such as fish oil or krill oil, for example, include cations such as $Fe^{+3}$ and thus cannot be mixed with GSH if the antioxidant activity of the GSH is to be preserved. It is nevertheless beneficial to consume such oils together with GSH because it is believed that such oils and GSH act synergistically to improve brain health.

In certain example embodiments, beneficial ingredients that negatively affect fatty acids can be separated from the fatty acids with the dual dosage form capsules described herein. As those skilled in the art will appreciate, copper and iron ions, for example, are strong chemical catalysts in the oxidation reaction of fish oil, resulting in toxicity of the fish oil. Such metal cations can also oxidize lutein and zeaxanthin, thus reducing the efficacy of these antioxidants. Current AREDI and AREDII (Age-Related Eye Disease Studies I & II) recommendations, however, indicate that in combining fish oil, lutein, Zeaxanthin, Copper, Zinc and vitamin C work synergistically to support eye health and prevent eye-related diseases such as age-related macular degeneration. Hence, multiple refinery processes—such as bleaching, steam deodorization, etc.—are used to reduce the level of these metals. The dual dosage form capsules, however, can be configured to include copper, zinc and/or vitamin C in the first fill material, while fish oil, lutein, and/or zeaxanthin can be included in the second fill material, thus providing for the delivery of multiple, beneficial ingredients.

In certain example embodiments, provided is a dual dosage form capsule that targets different regions of the gastro-intestinal system. For example, the first fill material may include an active ingredient that targets the stomach and/or small intestine, while the second fill material can include an active ingredient that targets the colon. That is, the first capsule member 20, 20', 20" or shell body 1 can be configured as described herein so that its contents are released in the stomach and/or small intestine. The second capsule member 30, 30", or shell body 2 can be configured so that the active ingredient is released in the colon, for example. In this way, one or more active ingredients can be targeted to different regions of the gastrointestinal system.

In certain example embodiments, provided is a dual dosage form capsule that includes two or more different probiotics. For example, the first fill material can include a probiotic that is targeted to the stomach, whereas the second fill material can include a probiotic that is targeted to the small intestine. Example probiotics that can be used with any of the dual dosage form capsule embodiments described herein include *Lactobacillus acidophilus, Lactobacillus ahamnosus, Lactobacillus helveticus, Bifidobacterium infantis, Bifidobacterium lactis, Lactobacillus bulgaricus, Lactobacillus silivarius, Lactobacillus plantarum, Lactobacillus reuteri, Lactobacillus casei, Bifidobacterum bifidum, Saccharomyces boulardii, Streptococcus thermophilus, Bifidobacterum breve, Bacillus coagulans, Lactobacillus brevis, Lactobacillus paracasei, Bifidobacterium longum, Lactobacillus johnsonii, Lactobacillus fermentum,* and *Pediococcus acidlacti*.

In certain example embodiments, the first fill material can include an antibiotic, such as amoxicillin, clarithromycin, and/or metronidazole, while the second fill material includes a probiotic. In certain example embodiments, the first fill material and the second fill material include different antibiotics. In certain example embodiments, the first fill material includes an antibiotic while the second fill material includes a proton pump inhibitor, such as omeprazole, lansoprazole, dexlansoprazole, esomeprazole, pantoprazole, rabeprazole, or ilaprazole.

In certain example embodiments, the dual dosage form capsules can include a probiotic in the first fill material and a prebiotic (or prebiotic rich foodstuff) in the second fill material. Such a configuration, for example, prevents the prebiotic from prematurely activating and/or affecting the probiotic before the dosage form is consumed. Example prebiotics include dietary fibers, such as polysaccharides and oligosaccharides, that can increase the number of probiotic organisms, which leads to the benefit conferred by the probiotic. The prebiotic can include, for example, an oligosaccharide, a fructo-oligosaccharide such as a soy fructo-oligosaccharide, inulin or banana fiber, a pectin or pectic polysaccharide, a mannan, such as guar gum, locust bean gum, konjac, or xanthan gum, a pentosan, beta-glucan, arabinan and galactan, such as larch arabinogalactan, and mixtures thereof. Other components that can support probiotics include, for example, colostrum and butyric acid. In certain example embodiments, the prebiotic is PreforPro™. In certain example embodiments, the probiotic is galactoooligosaccharide (GOS).

In certain example embodiments, such as softgels, heat is required to uniformly distribute the probiotic with the fill material of the softgel. As those skilled in the art will appreciate, however, heat can kill or inactivate the probiotic. The dual dosage form capsules address this issue by allowing, for example, the probiotic to be present in a different form, such as a powder, in one shell body 1 while another ingredient can be placed in the second shell body 2. Hence, heat is not needed to disperse the probiotic.

In certain example embodiments, provided is a dual dosage form capsule that reduces or prevents gas evolution. As those skilled in the art will appreciate, adding an acidic active ingredient to any carbonate solution can result in gas evolution. Potassium carbonate and sodium carbonate, for example, can react with Vitamin C to produce carbon dioxide. Sodium and potassium, however, aid in the absorption of Vitamin C (and Quercitin especially in the reduction of histamine), and hence are beneficially consumed with Vitamin C and Quercitin. Thus, provided is a dual dosage form capsule that includes a mineral carbonate, such as sodium or potassium carbonate, in the first fill material and an acidic active ingredient, such as vitamin C, in the second fill material.

Manufacturing the Capsule

The systems and devices for manufacturing the capsules include at least a capsule body filling device 100 (illustrated in FIG. 9) sized and configured to fill and seal the first and second capsule members 20, 20', 20", 30, 30" and various capsule halves described above and a capsule forming device 200 (illustrated in FIG. 10) sized and configured to couple the capsule members with the band 3, or shell bodies 1, 2, or capsule members with the first capsule members 20', 20", 30" to form the capsules. The capsule body filling device 100 and the capsule forming device 200 can be formed from rigid materials, such as metal, wood, ceramics, polymeric materials and the like.

Figure 9:
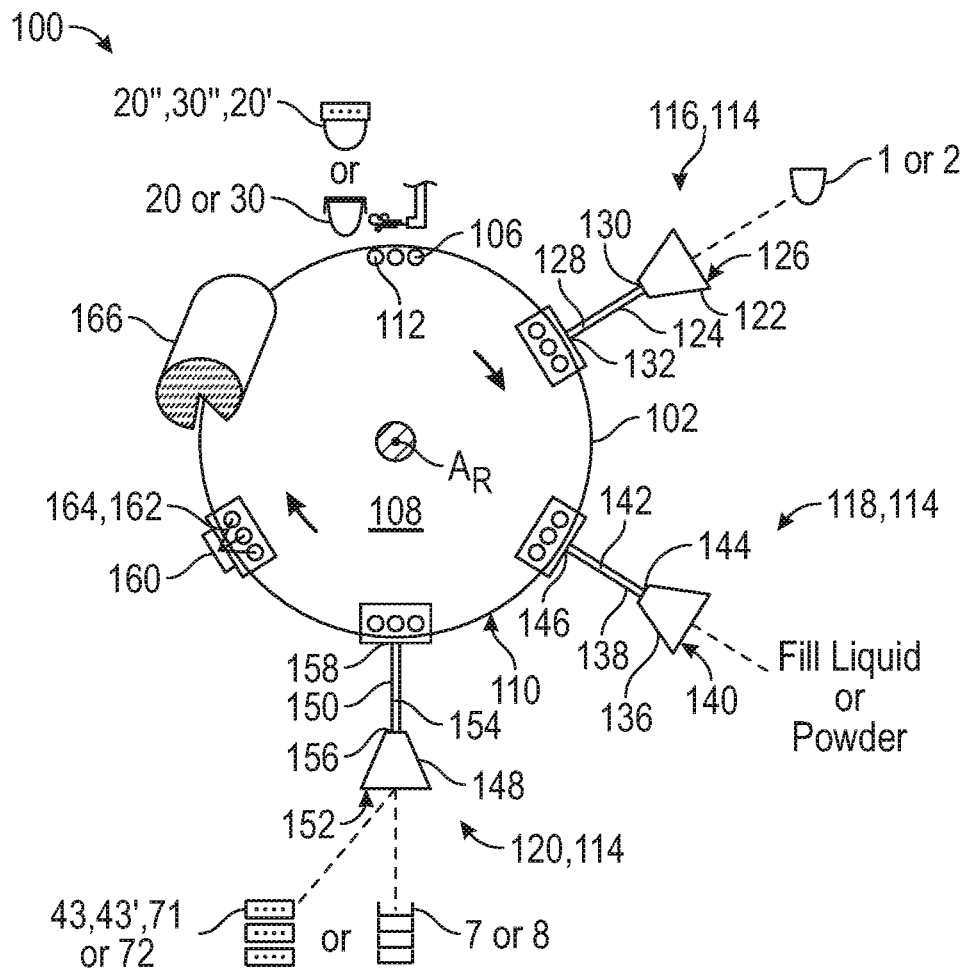
FIG. 9 is a schematic view of a capsule body filling device for manufacturing a dual release dosage form capsule.

Referring to FIG. 9, the capsule body filling device 100 includes a substantially planar rotating disc 102 sized and configured to hold and position a shell body 1, 2. For example, a plurality of pockets 106 defined in an upper surface 108 of the rotating disc are positioned adjacent to a perimeter 110 of the rotating disc. Each pocket 106 is sized and configured to hold at least a portion of a shell body 1, 2 therein. In one example, at least a portion of a pocket wall 112 can be arcuate in shape to correspond to the arcuate closed end 12, 22 of the shell body (see pocket wall 206 in FIG. 11). For example, at least a portion of the pocket wall can be semi-spherical so that the closed end of the shell body can be positioned in the pocket 106, with the open end 11, 21 of the shell body facing away from the rotating disc 102. The rotating disc 102 can have a rotational axis AR extending through the center of the disc. In certain example embodiments, the rotational axis of the rotating disc can be substantially normal to the upper surface 108 of the rotating disc (i.e. out of the page in FIG. 9).

The capsule body filling device 100 further includes a plurality of dispensing devices 114. For example, the plurality of dispensing devices can include at least one of a shell body dispenser 116, at least one pharmaceutical dispenser 118 and a cap or band dispenser 120. In certain example embodiments, the plurality of dispensing devices 114 can be positioned above the rotating disc 102 so that as the disc rotates, the pockets 106 can move adjacent to a portion of the desired dispensing device.

In certain example embodiments, the shell body dispenser 116 can be sized and configured to position a shell body 1, 2 in a pocket of the plurality of pockets 106 of the rotating disc 102. For example, the shell body dispenser includes a shell body hopper 122 and a shell body track 124. In one example, the shell body hopper can be a container sized and configured to hold a plurality of shell bodies 1, 2. That is, the shell body hopper 122 can have a storage chamber 126 for a plurality of shell bodies. In another example, the shell body track 124 can be configured to convey shell bodies 1, 2 from the shell body hopper to the rotating disc 102. For example, the shell body track can include a shell body tube 128 having a first end 130 coupled to the shell body hopper 122 and a second end 132 positioned adjacent a pocket 106 of the rotating disc. In use, the shell bodies in the shell body hopper can be gravity fed through an inner lumen of the tube and to a pocket 106 in the rotating disc 102. Optionally, the shell bodies 1, 2 can be pneumatically urged through the inner lumen of the shell body tube 128. For example, positive air pressure at the first end of the tube and/or negative air pressure (a vacuum) at the second end of the tube 128 can urge the shell bodies 1, 2 through the inner lumen of the tube and to a pocket in the rotating disc 102.

In certain example embodiments, the shell body track 124 can include a shell body conveyor, such as an endless conveyor belt and the like having a first end adjacent the shell body hopper 122 and a second end adjacent a pocket 106 in the rotating disc 102. In this example, the shell body conveyor can be sized and configured to carry shell bodies 1, 2 from the shell body hopper to the rotating disc.

In still another example embodiment, the shell body track 124 and/or the rotating disc 102 can be configured so that the shell bodies 1, 2 are positioned in a pocket 106 of the rotating disc with the closed end 12, 22 of the shell body contacting the upper surface 108 of the rotating disc 102 and with the open end 11, 21 of the shell body 1, 2 facing away from the rotating disc so that the distal edge 17, 27 of the first sidewall 13 or second sidewall 23 is spaced from the upper surface of the rotating disc a predetermined distance.

The pharmaceutical dispenser 118 can be sized and configured to insert a fill material 36, 37 into the respective first and second chambers 5, 6 of a shell body 1, 2 positioned in a pocket of the plurality of pockets 106 of the rotating disc 102. In one example embodiment, the pharmaceutical dispenser can include a pharmaceutical hopper 136 and a pharmaceutical track 138. In another example embodiment, the pharmaceutical hopper can be a container sized and configured to hold the fill material 36, 37, such as a pharmaceutical and the like therein. That is, the pharmaceutical hopper 136 can have a storage chamber 140 configured to hold a liquid fill material, a granular fill material, or a powder fill material as desired. The pharmaceutical track 138 can be configured to convey the fill material from the pharmaceutical hopper to the rotating disc 102. For example, the pharmaceutical track can include a pharmaceutical tube 142 having a first end 144 coupled to the pharmaceutical hopper 136 and a second end 146 positioned adjacent to a shell body 1, 2 in pocket 106 of the rotating disc. In use, the fill material 36, 37 in the pharmaceutical hopper can be gravity fed through an inner lumen of the pharmaceutical tube and through the open end 11, 21 in a shell body into the first and second chamber 5, 6 of a shell body 1, 2 in a pocket 106 in the rotating disc 102. Optionally, the fill material can be pneumatically urged through the inner lumen of the pharmaceutical tube 142. For example, positive air pressure at the first end of the tube and/or negative air pressure (a vacuum) at the second end of the tube 142 can urge the fill material through the inner lumen of the tube and to shell bodies 1, 2 in the rotating disc 102.

In certain example embodiments, the pharmaceutical track 138 can include a pharmaceutical conveyor, such as an endless conveyor belt and the like having a first end adjacent the pharmaceutical hopper 136 and a second end adjacent to a shell body 1, 2 in a pocket 106 of the rotating disc 102. In such examples, the pharmaceutical conveyor can be sized and configured to carry a fill material from the pharmaceutical hopper to the rotating disc 102.

Optionally, the pharmaceutical dispenser 118 can include a plurality of pharmaceutical dispensers. In certain example embodiments, a first pharmaceutical dispenser can be configured to deliver the first fill material 36 to the shell bodies 1, 2 in the rotating disc 102 and a second pharmaceutical dispenser can be configured to deliver a second fill material 37 to the shell bodies in the rotating disc, wherein the first fill material is the same or different than the second fill material. For example, the first pharmaceutical dispenser can be configured to deliver a liquid fill material to the shell bodies 1, 2 and the second pharmaceutical dispenser can be configured to deliver a powder fill material. Of course, it is contemplated that the plurality of pharmaceutical dispensers can include 3, 4, 5, 6, 7, 8, 9, 10 or more than 10 pharmaceutical dispensers, each pharmaceutical dispenser configured to deliver a fill material to the shell bodies in the rotating disc 102.

In certain example embodiments, the cap or band dispenser 120 can be sized and configured to position a cap such as the first cap 7 and the second cap 8 onto a shell body 1, 2 positioned in a pocket 106 of the rotating disc 102 or a band 43, 43', 71 or 72 onto a shell body 1, 2. For example, the cap or band dispenser includes a hopper 148 and a track 150. In one example embodiment, the hopper 148 can be a container sized and configured to hold a plurality of caps or bands. That is, the hopper 148 can have a storage chamber 152 for a plurality of caps or plurality of bands. In a further example embodiment, the track 150 can be configured to convey the caps or bands from the hopper to the rotating disc 102. For example, the track 150 can include a tube 154 having a first end 156 coupled to the hopper 148 and a second end 158 positioned adjacent pocket 106 of the rotating disc. In another example embodiment, the hopper 148 and/or the track 150 can be sized and configured to hold a plurality of caps or bands in a stacked position as illustrated in FIG. 9. In use, the caps or bands in the hopper 148 can be gravity fed through an inner lumen of the tube 154 and to a shell body 1, 2 in the rotating disc 102. Optionally, the caps or bands can be pneumatically urged through the inner lumen of the tube. For example, positive air pressure at the first end 156 of the tube and/or negative air pressure (a vacuum) at the second end 158 of the tube 154 can urge the caps or bands through the inner lumen of the tube and to a shell body in the rotating disc 102.

In certain example embodiments, the track 150 can include a conveyor, such as an endless conveyor belt and the like having a first end adjacent the hopper 148 and a second end adjacent to shell body 1 or 2 in the rotating disc 102. In such examples, the conveyor can be sized and configured to carry caps or bands from the hopper to the rotating disc.

The capsule body filling device 100 further includes a sealing device 160 configured to seal the cap 7, 8 or band 43, 43', 71 or 72 to a shell body 1 or 2 and form the respective capsule member 20, 20', 20", 30, 30". In one example embodiment, the sealing device includes at least one laser 162. In such examples, the laser can be a focused laser directed toward at least a portion of the cap and/or the shell body so that the laser 162 can heat seal the cap 7, 8 or band 43, 43', 71 or 72 to a shell body 1 or 2, thereby forming a capsule member. In another example embodiment, the laser can heat seal the cap or band to the shell body at a temperature of between about 70° F. and 120° F. Optionally, the laser 162 can heat seal the cap or band to the shell body 1, 2 at a temperature of between about 80° F. and 110° F. In a further example embodiment, the laser can include a plurality of lasers. Thus, as described more fully below, when the rotating disc 102 rotates with the caps and shell bodies positioned therein, each laser 162 of the plurality of lasers can be directed toward a cap or band and/or shell body 1, 2 at a predetermined rotational position.

In certain example embodiments, the sealing device 160 includes at least one heater 164. In this example embodiment, the heater can be a focused heater directed toward the cap 7, 8 or band 43, 43', 71 or 72 and/or the shell body 1, 2 so that the heater 164 can heat seal the cap or band to the shell body and form a capsule member. In certain example embodiments, the heater can heat seal the cap or band to the shell body 1, 2 at a temperature of between about 70° F. and 120° F. Optionally, the heater 164 can heat seal the cap or band to the shell body at a temperature of between about 80° F. and 110° F. In a further example embodiment, the heater can include a plurality of heaters. Thus, as described more fully below, when the rotating disc 102 rotates with the caps or band and shell bodies 1, 2 positioned therein, each heater 164 of the plurality of heater can be directed toward a cap or band and/or shell body at a predetermined rotational position.

The capsule body filling device 100 further includes a capsule member cooling device 166 configured to cool the filled, sealed capsule members 20, 20', 20", 30, 30". For example, the capsule member cooling device can include a chiller configured to direct chilled air or other chilled fluid toward the capsule members positioned in the rotating disc 102. In certain example embodiments, the cooling device 166 can be sized and configured so that at least a portion of the rotating disc 102 rotates between a portion of the cooling device. For example, the cooling device 166 can be a "C" shaped cooling device sized and configured so that at least a portion of the rotating disc rotates between a portion of the cooling device. In certain example embodiments, the cooling device 166 can cool the capsule member at a temperature of between about 35° F. and 65° F. Optionally, the cooling device can cool the capsule member at a temperature of between about 45° F. and 55° F.

Figure 10:
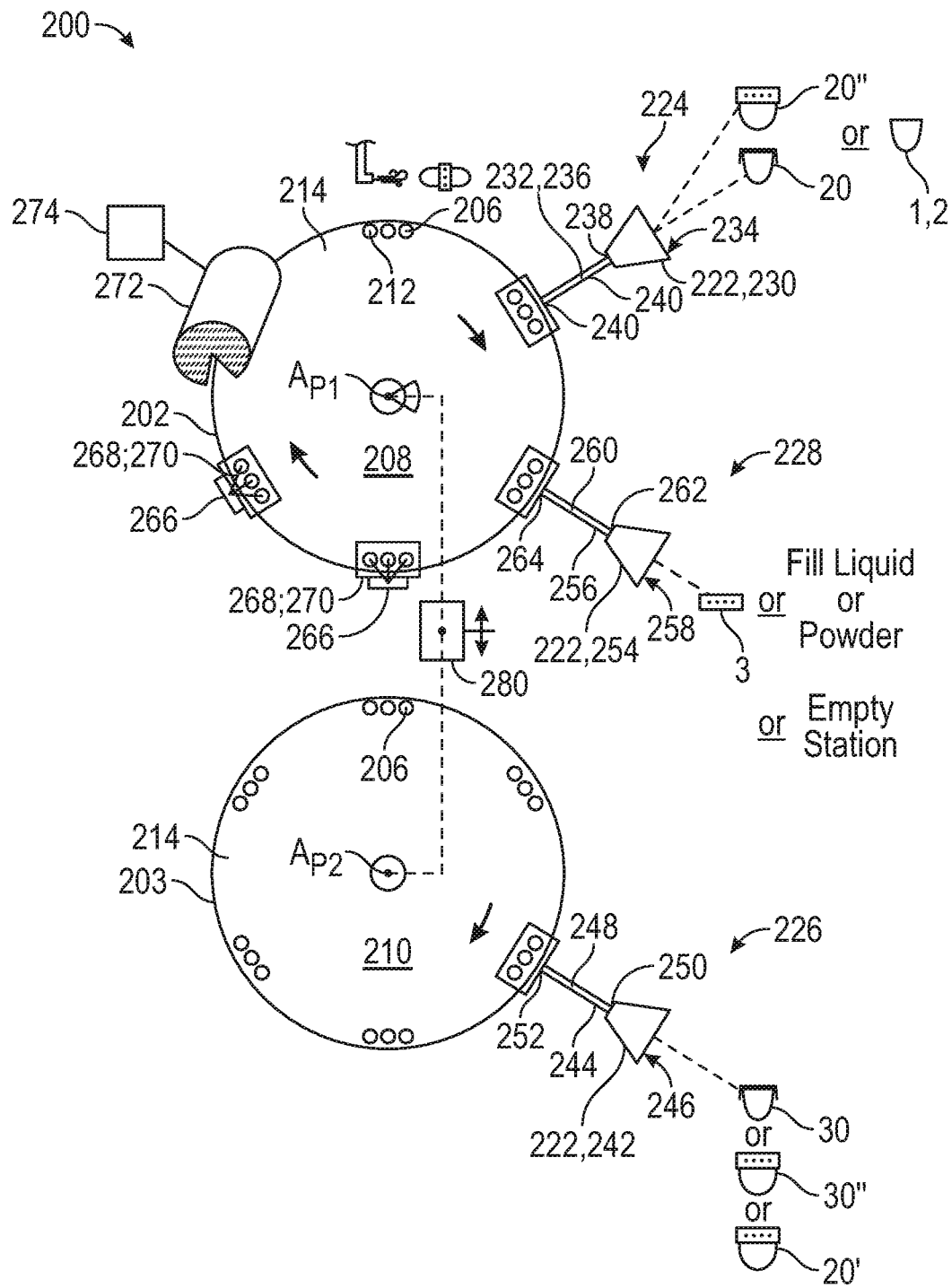
FIG. 10 is a schematic view of a capsule forming device for manufacturing a dual release dosage form capsule.

Referring now to FIG. 10, the capsule forming device 200 can be sized and configured to couple (i) a first capsule member 20 and a second capsule member 30 with the band 3 to form the capsule 10, (ii) an empty shell body 1, 2 that is filled with a fill material and a capsule member 20' having a band 43, 43' already sealingly connected thereto, (iii) a first capsule member 20 and a capsule member 20' having a band 43, 43' already sealingly connected thereto, or (iv) a first capsule member 20" and a second capsule member 30". At least portions of the capsule forming device can be formed from rigid materials, such as metal, wood, ceramics, polymeric materials and the like.

Sample configurations of rotating plates, filling mechanisms, and positive or negative pressure systems are described in U.S. Pat. Nos. 4,964,262 and 3,070,932. As representatively illustrated in FIG. 10, the capsule forming device 200 includes a pair of superimposed rotating plates, lower plate 202 and upper plate 203, wherein each rotating plate has a plurality of voids 206 sized and configured to hold a shell body 1 or 2 and/or capsule member 20, 20', 20", 30, or 30" therein. The lower plate 202 has an upper plate surface 208 and the upper plate 203 has a lower plate surface 210 facing one another. A plurality of voids 206 are defined in the upper surface 208 of the lower plate 202 and the lower plate surface 210 of the upper plate 203. In such examples, the plurality of voids 206 are positioned adjacent to a perimeter 214 of each rotating plate but are not limited thereto.

Figure 11:
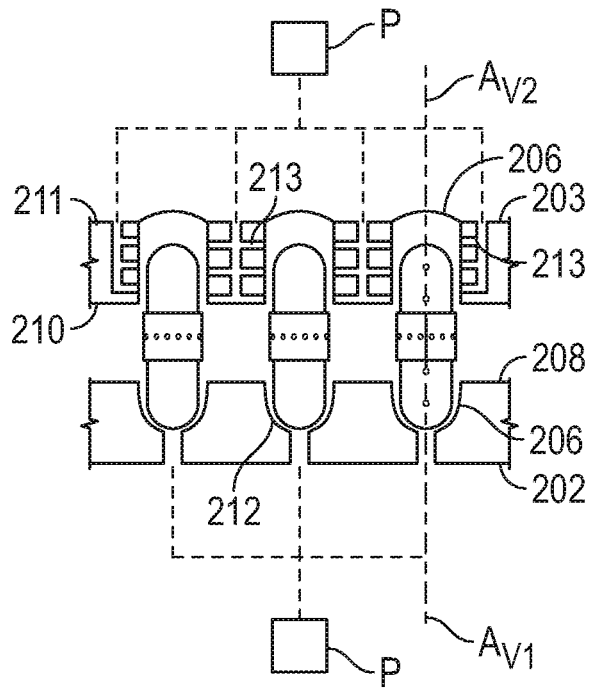
FIG. 11 is an enlarge partial view in a longitudinal cross-section through the capsule assembly station of a capsule forming device.

In the upper plate 203, the voids 206, as best seen in FIG. 11, pass through the plate as a bore from the lower plate surface 210 to the upper plate surface 211 and are dimensioned to receive a capsule member therethrough that has a cap or band sealingly connected thereto. As such, the capsule member can be introduced into the upper plate 203 through the upper plate surface 211 with the cap or band oriented toward to lower plate 202 (i.e., the cap or band enters the void 206 first). The upper plate 203 includes a plurality of pressure flow pathways 213 to each void 206 to apply negative pressure from a pressure source P to hold each capsule member in a predetermined position with the cap and/or band extending beyond the lower plate surface 210 toward the lower plate 202. In any embodiment where a shell body is to receive a cap or a capsule member is to receive a band, the shell body or capsule member should protrude beyond the lower plate surface 210 of the upper plate 203 or the upper plate surface 208 of the lower plate 202 by a distance in a range of 0.015 inch (0.38 mm) to 0.030 inch (0.76 mm).

As shown for the lower plate 202 in FIG. 11, at least a portion of a void wall 212 can be arcuate in shape to correspond to the closed end 12, 22 of the shell body 1, 2 of the capsule member. For example, at least a portion of the void wall 212 can be semi-spherical so that the closed end of the capsule member can be positioned in void 206, with the cap 7, 8 or band of the capsule member or an open end of the shell body 1, 2 facing away from the lower plate 202 in which it is positioned. In still another example embodiment, a vacuum can be applied to each void in the upper and/or lower plates 202, 203 to securely hold at least a portion of the capsule member within the void. Alternatively, gravity and/or a friction fit between the wall 212 of the void 206 and the capsule members or shell body can securely hold the same in the lower plate 202.

The lower plate 202 has a rotational axis $A_{P1}$ extending through the center thereof that is substantially normal to the upper plate surface 208 of the first plate 204, and the upper plate 203 has a rotational axis $A_{P2}$ extending through the center thereof that is substantially normal to the lower plate surface 210. The rotational axis $A_{P1}$ of the lower plate 202 and the rotational axis $A_{P2}$ of the upper plate 203 are co-axially aligned. In a first position, the lower plate 202 can be spaced from the upper plate 203 a predetermined distance that is the same distance around the perimeter 214 of the plates.

Figure 12:
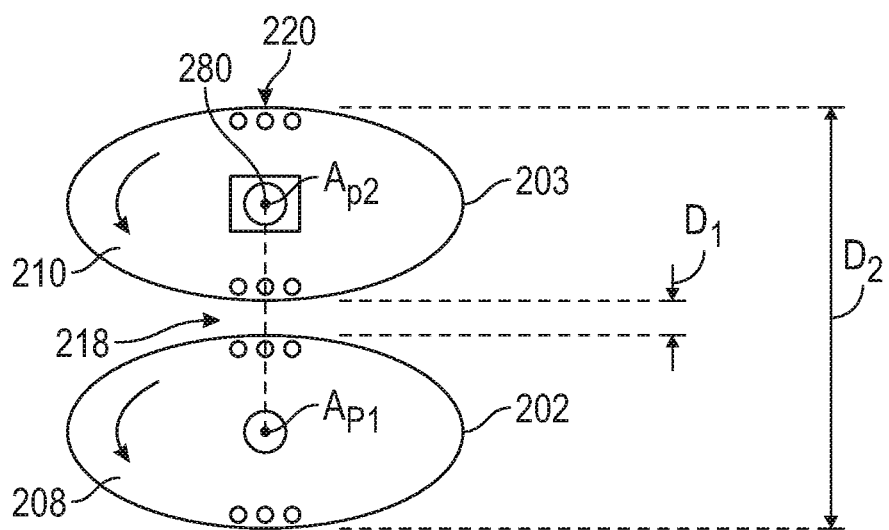
FIG. 12 is a schematic view of first and second rotating plates of the capsule forming device of FIG. 10, in accordance with certain example embodiments.

Referring to FIG. 12, the actuator 280 pivots the upper plate 203 or the lower plate 202 relative to the other (the upper plate 203 in FIG. 12) axially to move one plate position 218 toward the other plate and an opposing plate position 220 away from the other plate. The actuator 280 is also shown in FIG. 10 for further reference. With one of the plates 202 or 203 pivoted as such, the first plate position 218 has the plates spaced a distance apart $D_1$ and the second plate position 218 spaced apart a distance $D_2$, where $D_2$ is greater than $D_1$. The pivoting of one of the plates 202 or 203 can provide a downward or an upward force, respectively to push the capsule member(s) into or onto the band for a snap-fit, click-fit, interference fit, friction fit, or telescoping fit. Alternately or additionally, positive pressure can be applied using air flow to push the capsule member(s) toward the band. Also, the actuator 280 has the ability to lift the upper plate 203 or lower the lower plate 202 relative to the other plate such that assembled capsules are removed from the upper plate 203 and can rotate thereafter in just the lower plate 202 to subsequent sealing and cooling stations.

Figure 13:
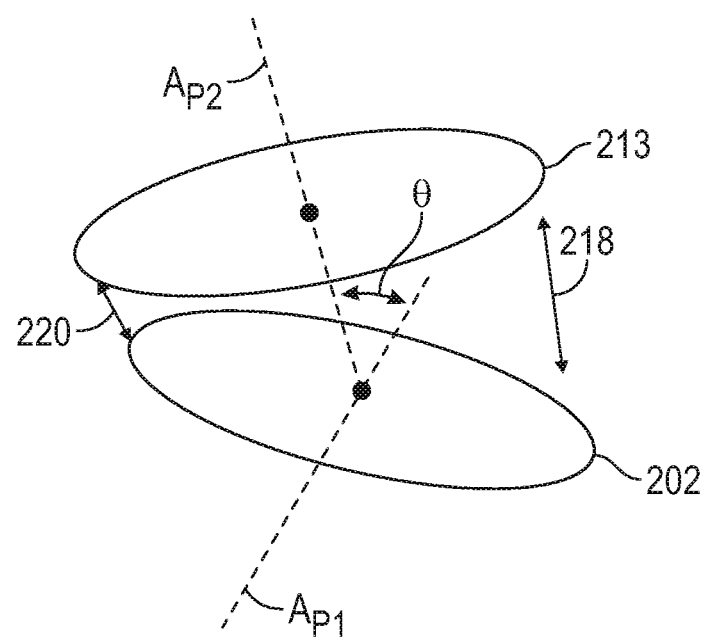
FIG. 13 is a schematic view of first and second rotating plates of another embodiment of a capsule forming device of FIG. 10.

Referring to FIG. 13, in another embodiment, the rotational axis $A_{P1}$ of the lower plate 202 can be at an acute angle θ relative to the rotational axis $A_{P2}$ of the upper plate 203 such that the upper surface 208 of the first plate is at an acute angle relative to the lower surface 210 of the second plate. In this example embodiment, the lower plate 202 can be spaced from the upper plate 203 a predetermined distance that varies around the perimeter 214 of the plates. For example, at a first plate position 218, the upper surface 208 of the lower plate 202 can be spaced a first predetermined distance from the lower surface 210 of the upper plate 203 and at a second plate position 220, the upper surface 208 of the lower plate 202 can be spaced a second predetermined distance from the lower surface 210 of the upper plate 203 that is less than the first plate position.

As can be appreciated, in one example embodiment, the rotational axis $A_{P1}$ of the lower plate 202 and/or the rotational axis $A_{P2}$ of the upper plate 203 can be substantially vertical as illustrated in FIGS. 11 and 12, such that at least one of the plates 202 rotates in a substantially horizontal plane. In another example embodiment, as illustrated in FIG. 13, the rotational axis $A_{P1}$ of the lower plate 202 and/or the rotational axis $A_{P2}$ of the upper plate 203 can be between vertical and horizontal such that at least one of the plates 202 rotates in a plane that is between horizontal and vertical. In still another example embodiment, the rotational axis $A_{P1}$ of the lower plate 202 and/or the rotational axis $A_{P2}$ of the upper plate 203 can be substantially horizontal (not illustrated), such that at least one of the plates 202 rotates in a substantially vertical plane.

In certain plate positions, each void 206 in the upper surface 208 of the lower plate 202 can be aligned with a void in the lower surface 210 of the upper plate 203. A longitudinal axis $A_{V1}$ of each void in the lower plate 202 can be substantially coaxially aligned with a longitudinal axis $A_{V2}$ of each void in the upper plate 203 for at least one plate position or for a portion of a revolution of the upper and lower plates 202, 203. Thus, in use as described more fully below, a first capsule member positioned in a void 206 in the upper surface 208 of the lower plate 202 can be aligned with a second capsule member positioned in a void in the lower surface 210 of the upper plate 203.

For example, if the rotational axis $A_{P1}$ of the lower plate 202 is at an acute angle relative to the rotational axis $A_{P2}$ of the upper plate 203, the longitudinal axis $A_{V1}$ of a void 206 in the first plate can be substantially coaxially aligned with the longitudinal axis $A_{V2}$ of a void in the second place for at least a portion of the revolution of the plates. In another example, if the rotational axis $A_{P1}$ of the lower plate 202 is at an acute angle relative to the rotational axis $A_{P2}$ of the upper plate 203, the longitudinal axis $A_{V1}$ of a void 206 in the first plate can be substantially coaxially aligned with the longitudinal axis $A_{V2}$ of a void in the second plate, with the first and second plates at any position about and between the first plate position 218 and the second plate position 220.

The capsule forming device 200 further includes a plurality of distribution devices 222. For example, the plurality of distribution devices can include at least one first capsule member or shell body distributor 224, a second capsule member distributor 226, and a band or fill distributor 228. In one example embodiment, the plurality of distribution devices 222 can be positioned adjacent the plurality of rotating plates 202, 203 so that as the plates rotate, the voids 206 in the plates can move adjacent to the desired distribution device.

The first capsule member distributor 224 can be sized and configured to position the first capsule member 20 or 20" or a shell body 1, 2 in a void 206 of the plurality of voids of the first rotating plate 204. For example, the first capsule member distributor includes a first hopper 230 and a first track 232. In certain example embodiments, the first hopper can be a container sized and configured to hold a plurality of first capsule members 20 or 20" or a shell body 1, 2. That is, the first hopper 230 can have a storage chamber 234 for a plurality of first capsule members or shell bodies. In another example embodiment, the first track 232 can be configured to convey first capsule members 20 or 20" or a shell body 1, 2 from the first hopper to the lower plate 202. For example, the first track 232 can include a first tube 236 having a first end 238 coupled to the first capsule member hopper 230 and a second end 240 positioned adjacent void(s) 206 of the first rotating plate. In use, the first capsule members 20 or 20" or a shell body 1, 2 in the first hopper can be gravity fed through an inner lumen of the first tube and to void(s) 206 in the upper surface 208 of the lower plate 202. Optionally, the first capsule member 20 or 20" or a shell body 1, 2 can be pneumatically urged through the inner lumen of the first tube 236. For example, positive air pressure at the first end of the tube and/or negative air pressure (a vacuum) at the second end of the first tube 236 can urge the first capsule member 20 or 20" or a shell body 1, 2 through the inner lumen of the tube and to a void in the lower plate 202.

In another example embodiment, the first track 232 can include a first conveyor, such as an endless conveyor belt and the like having a first end adjacent the first hopper 230 and a second end adjacent a void 206 in the lower plate 202. In this example embodiment, the first conveyor can be sized and configured to carry first capsule members 20, 20" or a shell body 1, 2 from the first hopper to the lower plate 202.

The second capsule member distributor 226 can be sized and configured to position the second capsule member 20', 30, or 30" in void(s) 206 of the upper plate 203. For example, the second capsule member distributor 226 includes a second hopper 242 and a second track 244. In one example embodiment, the second hopper 242 can be a container sized and configured to hold a plurality of second capsule members 20', 30, or 30". That is, the second hopper 242 can have a storage chamber 246 for a plurality of second capsule members 20', 30, or 30". In another example embodiment, the second track 244 can be configured to convey second capsule members 20', 30, or 30" from the second hopper to the upper plate 203. For example, the second track can include a second tube 248 having a first end 250 coupled to the second hopper 242 and a second end 252 positioned adjacent a void 206 of the upper plate 203. In use, the second capsule members 20', 30, or 30" in the second hopper can be gravity fed through an inner lumen of the second tube and to void(s) 206 in the lower surface 210 of the upper plate 203. Optionally, the second capsule member 20', 30, or 30" can be pneumatically urged through the inner lumen of the second tube 248. For example, positive air pressure at the first end of the tube and/or negative air pressure (a vacuum) at the second end of the tube 248 can urge the second capsule member 20', 30, or 30" through the inner lumen of the tube and to void(s) 206 in the upper plate 203.

In another example embodiment, the second track 244 can include a second capsule member conveyor, such as an endless conveyor belt and the like having a first end adjacent the second hopper 242 and a second end adjacent a void 206 in the upper plate 203. In this example embodiment, the second conveyor can be sized and configured to carry second capsule members 20', 30, or 30" from the second hopper to the upper plate 203.

A third distributor 222 may be present to distribute bands 2, a fill liquid or fill powder, or may be empty. When capsule members being assembled are the first and second capsule members 20 and 30, the third distributor 222 is a band distributor 228 which is sized and configured to position the band 3 around one of the first and second capsule members 20, 30, whichever is in the lower plate 202. For example, the band distributor 228 includes a third hopper 254 and a third track 256. In certain example embodiments, the third hopper 254 can be a container sized and configured to hold a plurality of bands 3. That is, the third hopper 254 can have a storage chamber 258 for a plurality of bands. In another example embodiment, the third track 256 can be configured to convey bands 3 from the third hopper to the first and second capsule members 20, 30. For example, the third track can include a band tube 260 having a first end 262 coupled to the third hopper 254 and a second end 264 positioned adjacent a first capsule member 20 in the lower plate 202 and a second capsule member 30 in the upper plate 203. In use, the bands 3 in the third hopper can be gravity fed through an inner lumen of the band tube 260 and to a first and second capsule members in the lower plate 202 and upper plate 203. Optionally, the bands 3 can be pneumatically urged through the inner lumen of the band tube 260. For example, positive air pressure at the first end of the tube and/or negative air pressure (a vacuum) at the second end of the tube 260 can urge the bands 3 through the inner lumen of the tube and to a first and second capsule members in the lower plate 202 and upper plate 203.

In another example embodiment, the third track 256 can include a band conveyor, such as an endless conveyor belt and the like having a first end adjacent the band 254 and a second end adjacent a first capsule member 20 in the lower plate 202 and a second capsule member 30 in the upper plate 203. In this example embodiment, the band conveyor can be sized and configured to convey bands 3 from the third hopper 254 to one of first and second capsule member 20, 30, whichever is in the lower plate 202.

The capsule forming device 200 further includes a capsule sealing device 266 configured to seal the band 3 to the first and second capsule members and form the capsule. The capsule sealing device 266 may be at the station where the two halves of the capsule are mated or at a station subsequent to the station where the two halves of the capsule are mated as illustrated in FIG. 10 but does not need to be at both stations. In certain example embodiments, the capsule sealing device 266 includes at least one capsule sealing laser 268. In this example embodiment, the capsule sealing laser can be a focused laser directed toward the band and/or the capsule members so that the capsule sealing laser 268 can heat seal the band or band portions to the capsule members and/or the band portions to one another thereby forming a capsule. In another example embodiment, the capsule sealing laser can heat seal the band or band portions to the capsule members at a temperature of between about 70° F. and 120° F. Optionally, the capsule sealing laser 268 can heat seal the band or band portions to the capsule members at a temperature of between about 80° F. and 110° F. In a further example embodiment, the at least one capsule sealing laser can include a plurality of capsule sealing lasers. Thus, as described more fully below, when the lower plate 202 rotate with the band and the capsule members positioned therein, each capsule sealing laser 268 of the plurality of lasers can be directed toward the band and/or capsule member at a predetermined rotational position.

In certain example embodiments, the capsule sealing device 266 includes at least one capsule sealing heater 270. In this example embodiment, the at least one capsule sealing heater can be a focused heater directed toward the band and/or the capsule members so that the capsule sealing heater 270 can heat seal the band to the capsule members or band portions to one another to form a capsule. In another example embodiment, the capsule sealing heater can heat seal the band to the capsule members or band portions at a temperature of between about 70° F. and 120° F. Optionally, the capsule sealing heater 270 can heat seal the band to the capsule members or band portions at a temperature of between about 80° F. and 110° F. In a further example embodiment, the at least one capsule sealing heater includes a plurality of capsule sealing heaters. Thus, as described more fully below, when the lower plate 202 rotates with the band and the capsule members positioned therein, each capsule sealing heater of the plurality of capsule sealing heater can be directed toward a band and/or capsule member at a predetermined rotational position.

The capsule forming device 200 further includes a capsule cooling device 272 configured to cool the assembled, sealed capsule. For example, the capsule cooling device can include a capsule chiller 274 configured to direct chilled air or other chilled fluid toward the capsule(s) positioned in at least the lower plate 202. In certain example embodiments, the capsule cooling device 272 can be sized and configured so that at least a portion of the capsule rotates between a portion of the capsule cooling device. For example, the capsule cooling device 272 can be a "C" shaped capsule cooling device sized and configured so that at least a portion of at least the lower plate rotate between a portion of the capsule cooling device. In certain example embodiments, the capsule cooling device can cool the capsule(s) at a temperature of between about 35° F. and 65° F. Optionally, the capsule cooling device 272 can cool the capsule(s) at a temperature of between about 45° F. and 55° F.

Referring back to FIG. 9, to form the first capsule member 20 of the dual release dosage form capsule 10, the first shell body 1 can be provided to and loaded into the shell body hopper 122, the first fill material 36 can be provided to and loaded into the at least one pharmaceutical hopper 136 and the first cap 7 can be provided to and loaded into the cap hopper 148. The first shell body can be urged down the shell body track 124 from the shell body hopper 122 to a pocket 106 of the rotating disc 102 with the first open end 11 of the first shell body facing away from the rotating disc. For example, the first shell body can be urged over the shell body track by gravity, pneumatically or mechanically. The rotating disc 102 can rotate so that the open end 11 of the first shell body 1 is adjacent to a portion of the pharmaceutical track 138.

The first fill material 36 can be urged down the pharmaceutical track 138 from the pharmaceutical hopper 136, through the open end 11 of the first shell body 1 and into the first chamber 5 of the first shell body. For example, the first fill material can be urged over the pharmaceutical track by gravity, pneumatically or mechanically and into the first chamber of the first shell body 1. The rotating disc 102 can then rotate so that the open end 11 of the first shell body 1 is adjacent to a portion of the cap track 150.

The first cap 7 can be urged down the cap track 138 from the cap hopper 148 and positioned over the open end 11 of the first shell body 1. For example, a portion of the first cover 14 and/or the first lip of the first cap 7 can engage a distal edge 17 of the first sidewall 13 of the first shell body 1 to enclose the first fill material 36 in the first chamber 5. That is, at least a portion of the first cap can be in contact with the first shell body to enclose the first fill material inside the first chamber. In certain example embodiments, the first cap 7 can be urged over the cap track by gravity, pneumatically or mechanically. The rotating disc 102 can then rotate so that the first shell body 1, the first fill material 36 and the first cap 7 are positioned adjacent to and/or aligned with the sealing device 160.

In certain example embodiments, if the sealing device 160 includes at least one laser 162, the rotating disc 102 can rotate until the first shell body 1 and/or the first cap 7 are aligned with the laser so the laser can seal the first cap to the first shell body, forming the first capsule member 20. In another example embodiment, if the sealing device includes at least one heater 164, the disc can rotate until the first shell body 1 and/or the first cap 7 are positioned to receive heat from the heater 164 so the heat can seal the first cap to the first shell body, forming the first capsule member 20. The rotating disc 102 can then rotate so that the first capsule member 20 is positioned adjacent to and/or aligned with the capsule member cooling device 166.

In certain example embodiments, if the capsule member cooling device 166 includes a chiller, the rotating disc 102 can rotate until the first capsule member is positioned to be chilled with fluid or air from the chiller to cool the first member 20 to the desired temperature. Upon reaching the desired temperature, the first member can be discharged from the rotating disc 102 by gravity, pneumatically or mechanically.

As can be appreciated, a plurality of first shell bodies 1, first fill materials 36 and first caps 7 can be provided to the respective hoppers, so that the capsule body filling device can produce a plurality of first capsule members 20 quickly and inexpensively compared to manual methods of forming the first capsule member.

To form the second capsule member 30 of the dual release dosage form capsule 10, the process above is repeated. The second shell body 2 can be provided to and loaded into the shell body hopper 122, the second fill material 37 can be provided to and loaded into the at least one pharmaceutical hopper 136 and the second cap 8 can be provided to and loaded into the cap hopper 148. The second shell body can be urged from the shell body hopper 122 down the shell body track 124 to a pocket 106 of the rotating disc 102 with the open end 21 of the second shell body facing away from the rotating disc. For example, the second shell body 2 can be urged over the shell body track by gravity, pneumatically or mechanically. The rotating disc 102 can then rotate so that the open end 21 of the second shell body is adjacent to a portion of the pharmaceutical track 138.

The second fill material 37 can be urged down the pharmaceutical track 138, from the pharmaceutical hopper 136, through the open end 21 of the second shell body 2 and into the second chamber 6 of the second shell body. For example, the second fill material can be urged over the pharmaceutical track by gravity, pneumatically or mechanically. The rotating disc 102 can then rotate so that the open end 21 of the second shell body 21 is adjacent to a portion of the cap track 150.

The second cap 8 can be urged down the cap track 138 from the cap hopper 148 and positioned over the open end 21 of the second shell body 2. For example, a portion of the second cover 24 and/or the second lip 25 of the second cap 8 can engage a distal edge 27 of the second sidewall 23 of the second shell body 2 to enclose the second fill material 37 in the second chamber 6. That is, at least a portion of the second cap can be in contact with the second shell body to enclose the second fill material inside the second chamber. In certain example embodiments, the second cap 8 can be urged over the cap track by gravity, pneumatically or mechanically. The rotating disc 102 can then rotate so that the second shell body 2, the second fill material 37 and the second cap 8 are positioned adjacent and/or aligned with the sealing device 160.

In certain example embodiments, if the sealing device 160 includes at least one laser 162, the rotating disc 102 can rotate until the second shell body 2 and/or the second cap 8 are aligned with the laser so the laser can seal the second cap to the second shell body, forming the second capsule member 30. In another example embodiment, if the sealing device includes at least one heater 164, the disc can rotate until the second shell body 2 and/or the second cap 8 are positioned to receive heat from the heater 164 so the heat can seal the second cap to the second shell body, forming the second capsule member 30. The rotating disc 102 can then rotate so that the second capsule member 30 is positioned adjacent and/or aligned with the capsule member cooling device 166.

In certain example embodiments, if the capsule member cooling device 166 includes a chiller, the rotating disc 102 can rotate until the second capsule member 30 is positioned to be chilled with fluid or air, from the chiller to cool the second capsule member to the desired temperature. Upon reaching the desired temperature, the second capsule member 30 can be discharged from the rotating disc 102 by gravity, pneumatically or mechanically.

As can be appreciated, a plurality of second shell bodies 2, second fill materials 37 and second caps 8 can be provided to the respective hoppers so that the capsule body filling device 100 can produce a plurality of second capsule members 30 quickly and inexpensively compared to manual methods of forming the second capsule member.

Still referring to FIG. 9, the process described above for the first capsule member 20 or the second capsule member 30 is repeatable to form one of the other capsule members disclosed herein by introducing a band 43, 43', 71 or 72 at the cap or band dispenser 120 to form capsule members 20', 20", or 30".

Referring to FIG. 10, to illustrate the formation of the dual release dosage form capsule 10 of FIG. 2, the capsule forming device 200 couples the first capsule member 20 to the second capsule member 30 with the band 3. The first capsule member 20 is provided to and loaded into the first hopper 230, the second capsule member 30 is provided to and loaded into the second hopper 242 and the band 3 is provided to and loaded into the third hopper 254. The first capsule member 20 is urged down the first track 232 from the first capsule member hopper 230 to a void 206 of the lower plate 202 with the first cap 7 of the first capsule member facing away from the first rotating plate. The first capsule member 20 can be urged over the first track by gravity, pneumatically or mechanically.

The second capsule member 30 can be urged down the second track 232 from the second hopper 242 to a void 206 of the upper plate 203 with the second cap 8 of the second capsule member facing away from the upper plate. The second capsule member 30 can be urged over the second track by gravity, pneumatically or mechanically.

The band 3 is urged down the third track 256 from the third hopper 254 to the first and second capsule members 20, 30 positioned in the respective upper and lower plates 202, 203. The band 3 can be urged over the band track by gravity, pneumatically or mechanically. In certain example embodiments, a portion of the first capsule member 20 can be inserted through the first entry port 34 of the band 3 and into the passage 33 of the band, and a portion of the second capsule member 30 can be inserted through the second entry port 35 and into the passage of the band 3. In the passage, the first capsule member can be spaced from the second capsule member a predetermined distance to form the third chamber 4.

The lower plate 202 and the upper plate 203 can rotate simultaneously (i.e. at the same velocity and at the same time) to move the first capsule member 20, the second capsule member 30 and the band 3 to a position adjacent and/or aligned with the capsule sealing device 266 or the plates 202, 203 can separate using the actuator 280 such that just the lower plate 202 retains the capsule and rotates to the capsule sealing device 266. The capsule sealing device can direct heat towards the band 3 and/or the capsule members 20, 30 to seal the band to the first and second capsule members 20, 30 and form the capsule 10. For example, if the capsule sealing device 266 includes at least one capsule laser 268, the upper and lower plates 202, 203 can rotate until the band 3 and/or the capsule members 20, 30 are aligned with the capsule laser so the capsule laser can seal the band to the first and second capsule members 20, 30, forming the capsule 10. In another example embodiment, if the capsule sealing device includes at least one capsule heater 270, the upper and lower plates 202, 203 can rotate until the band 3 and/or the capsule members 20, 30 are positioned to receive heat from the capsule heater so the heat can seal the band 3 to the first and second capsule members 20, 3, forming the capsule 10. The upper and lower plates 202, 203 can then rotate so that the capsule is positioned adjacent and/or aligned with the capsule cooling device 272.

In certain example embodiments, if the capsule cooling device 272 is a capsule chiller, the upper and lower plates 202, 203 can rotate until the capsule 10 is positioned to be chilled with fluid or air from the capsule chiller to cool the capsule to the desired temperature. Upon reaching the desired temperature, the capsule 10 can be discharged from the upper and lower plates 202, 203 by gravity, pneumatically or mechanically.

As can be appreciated, a plurality of first capsule members 20, second capsule members 30 and bands 3 can be provided to the respective hoppers so that the capsule forming device 200 can produce a plurality of capsules quickly and inexpensively compared to manual methods of forming the capsule 10.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the art will recognize and understand. For example, while processes can be presented in a given order, alternative embodiments can perform routines having steps in a different order, with some steps being deleted, moved, added, subdivided, combined, and/or modified to provide alternative or sub-combinations. Each of these processes can be implemented in a variety of different ways, as those skilled in the art will appreciate. Also, while processes are at times shown as being performed in series, these processes can instead be performed in parallel, or can be performed, at different times. Further, any specific numbers noted herein are only examples—alternative implementations can employ differing values or ranges.

The teachings of the disclosure provided herein can be applied to other systems, not necessarily the system described above. The elements and acts of the various embodiments described above can be combined to provide further embodiments. Any patents noted above that are incorporated herein by reference, for example, can be modified, as necessary, to provide yet further embodiments of the disclosure provided herein. Further, while the above description describes certain embodiments, the teachings can be practiced in many ways that will be appreciated by those of skill in the art no matter how detailed the above appears in text. Details of the capsule members, capsules, and related processes and products can vary considerably in their implementation details, while still being encompassed by the subject matter disclosed herein. Hence, although example embodiments of the invention have been shown and described, it is to be understood that all the terms used herein are descriptive rather than limiting, and that many changes, modifications, and substitutions can be made by one having skill in the art without departing from the spirit and scope of the claims below.

What is claimed is:

1. A capsule forming machine comprising:
   a first capsule body filling device comprising:
   a rotating plate defining a plurality of voids for receiving a first shell body of a capsule, wherein the plurality of voids define a plurality of stations located adjacent to a perimeter of the rotating plate;

a first dispenser configured to position the first shell body of the capsule in each of the plurality of voids at a first of the plurality of stations;

a second dispenser configured to insert a fill material into the shell body in each of the plurality of voids at a second of the plurality of stations;

a third dispenser configured to position (i) a cap, (ii) a band comprising a cap, (iii) a first band portion comprising a cap, or (iv) a second band portion comprising a cap onto the shell body in each of the plurality of voids at a third of the plurality of stations;

a sealing device configured to seal the cap or band comprising a cap to a respective shell body to form a sealed capsule member with the filling material therein; and a capsule forming device comprising:

superimposed upper and lower plates that are each rotatable about an axis of rotation, the axis of rotation extending through the center of each plate and being co-axially aligned with one another; wherein each of the upper and lower plates define a plurality of voids for receiving a shell body or a capsule member of a capsule that are positioned to define a plurality of stations located adjacent to a perimeter of the respective upper plate and lower plate;

wherein the lower plate comprises a first lower plate dispenser configured to position a sealed capsule member formed by the first capsule filling device in each of the plurality of voids a first of the plurality of lower stations;

wherein the upper plate comprises a first upper plate dispenser configured to position a sealed capsule member formed by the first capsule filling device in each of the plurality of voids at a first of a plurality of upper stations;

an actuator operatively connected to either of the upper or lower plates, wherein the actuator lifts and lowers the upper plate or the lower plate relative to the other plate and/or pivots the upper plate or the lower plate relative to the other plate transverse to the rotational axis to move a capsule assembly station of the plurality of stations thereof toward to the other plate and then away from the other plate at predetermined times, wherein the capsule assembly station is configured to mate the sealed capsule member in the upper plate and the sealed capsule member in the lower plate together to form a capsule having filling material in each sealed capsule member; and a sealing device operatively positioned at either the capsule assembly station or a station subsequent to the capsule assembly station, wherein the sealing device comprises a heater configured to form a heat seal.

2. The machine of claim 1, further comprising a cooling device operative positioned subsequent to the sealing device.

3. The machine of claim 1, wherein the third dispenser of the first capsule body filling device is configured to position a cap onto the shell body in each of the plurality of voids at a third of the plurality of stations, and wherein the capsule forming device further comprises a second dispenser configured to position a band on each of the sealed capsule members in each of the plurality of voids at a second of the plurality of stations of the lower plate.

4. The machine of claim 1, wherein the sealed capsule members in the upper plate have the first band portion comprising the cap and the first sealed capsule members in the lower plate have the second band portion comprising the cap, wherein at the capsule assembly station the first band portion and the second band portion are mated together to form a capsule.

5. The machine of claim 1, wherein the heater comprises a focused laser.

6. The machine of claim 5, wherein the focused laser forms a heat seal to the shell body or capsule member at a temperature of between 70° F. to 120° F.

7. The machine of claim 1, wherein the third dispenser of the first capsule body filling device is configured to position the band comprising the cap and first dispenser of the lower plate is configured to position the sealed capsule member having the cap in each of the plurality of voids of the first of the plurality of stations.

8. A capsule forming machine comprising:

a first capsule body filling device comprising:

a rotating plate defining a plurality of voids for receiving a first shell body of a capsule, wherein the plurality of voids define a plurality of stations located adjacent to a perimeter of the rotating plate;

a first dispenser configured to position the first shell body of the capsule in each of the plurality of voids at a first of the plurality of stations;

a second dispenser configured to insert a fill material into the first shell body of the capsule in each of the plurality of voids at a second of the plurality of stations;

a third dispenser configured to position (i) a cap, (ii) a band comprising the cap, or (iii) a first band portion comprising the cap onto the first shell body of the capsule in each of the plurality of voids at a third of the plurality of stations;

a sealing device configured to seal the cap to a respective shell body to form a sealed capsule member with the filling material therein; and a capsule forming device comprising:

superimposed upper and lower plates that are each rotatable about an axis of rotation, the axis of rotation extending through the center of each plate and being co-axially aligned with one another; wherein the lower plate defines a plurality of voids for receiving a second shell body or a capsule member of a capsule that are positioned to define a plurality of stations located adjacent to a perimeter of the lower plate and the upper plate defines a plurality of voids for receiving a capsule member that are position positioned to define a plurality of stations located adjacent to a perimeter of the upper plate;

wherein the lower plate comprises a first lower plate dispenser configured to position the second shell body of a capsule in each of the plurality of voids a first of the plurality of lower stations, and a second dispenser configured to insert a fill material into the second shell body of the capsule in each of the plurality of voids at a second of the plurality of lower stations;

wherein the upper plate comprises a first upper dispenser configured to position a sealed capsule member formed by the first capsule filling device in each of the plurality of voids at a first of a plurality of upper stations;

an actuator operatively connected to either of the upper or lower plates, wherein the actuator lifts and lowers the upper plate or the lower plate relative to the other plate and/or pivots the upper plate or the lower plate relative to the other plate transverse to the rotational axis to move a capsule assembly station of the plurality of stations thereof toward to the other plate and then away from the other plate at predetermined times, wherein the capsule assembly station is configured to mate filled second shell body in the lower plate and the sealed capsule member in the upper plate together to form a capsule having filling material in each of the first shell body and the second shell body; and a sealing device operatively positioned at either the capsule assembly station or a station subsequent to the capsule assembly station, wherein the sealing device comprises a heater configured to form a heat seal.

9. The machine of claim 8, wherein the heater comprises a focused laser.

10. The machine of claim 9, wherein the focused laser forms a heat seal to the shell body or capsule member at a temperature of between 70° F. to 120° F.

11. The machine of claim 8, further comprising a cooling device operative positioned subsequent to the sealing device.

\* \* \* \* \*